US008986968B2

(12) United States Patent
Clark et al.

(10) Patent No.: US 8,986,968 B2
(45) Date of Patent: Mar. 24, 2015

(54) THERMOSTABLE DNA POLYMERASE

(75) Inventors: Duncan Clark, Camberley (GB); Nicholas Morant, Camberley (GB)

(73) Assignee: Genesys Biotech Ltd. (GB)

( * ) Notice: Subject to any disclaimer, the term of this patent is extended or adjusted under 35 U.S.C. 154(b) by 343 days.

(21) Appl. No.: 12/919,622

(22) PCT Filed: Feb. 13, 2009

(86) PCT No.: PCT/GB2009/000411
§ 371 (c)(1),
(2), (4) Date: Aug. 26, 2010

(87) PCT Pub. No.: WO2009/106795
PCT Pub. Date: Sep. 3, 2009

(65) Prior Publication Data
US 2011/0008848 A1    Jan. 13, 2011

(30) Foreign Application Priority Data
Feb. 28, 2008 (GB) .................................. 0803628.7

(51) Int. Cl.
*C12N 9/12* (2006.01)
(52) U.S. Cl.
CPC .................................. *C12N 9/1252* (2013.01)
USPC ......................................... 435/194; 435/183
(58) Field of Classification Search
None
See application file for complete search history.

(56) References Cited

U.S. PATENT DOCUMENTS

| | | | |
|---|---|---|---|
| 4,889,818 A | 12/1989 | Gelfand et al. |
| 4,952,496 A | 8/1990 | Studier et al. |
| 4,965,188 A | 10/1990 | Mullis et al. |
| 5,047,342 A | 9/1991 | Chatterjee |
| 5,079,352 A | 1/1992 | Gelfand et al. |
| 5,270,179 A | 12/1993 | Chatterjee |
| 5,374,553 A | 12/1994 | Gelfand et al. |
| 5,436,149 A | 7/1995 | Barnes |
| 5,512,462 A | 4/1996 | Cheng |
| 5,614,365 A | 3/1997 | Tabor et al. |
| 5,616,494 A | 4/1997 | Barnes |
| 5,677,152 A | 10/1997 | Birch et al. |
| 5,834,285 A | 11/1998 | Comb et al. |
| 6,627,424 B1 | 9/2003 | Wang |
| 7,045,328 B2 | 5/2006 | Mathur |
| 7,704,713 B2 | 4/2010 | Sato et al. |
| 2007/0141591 A1 | 6/2007 | Borns |
| 2011/0014660 A1 | 1/2011 | Clark et al. |
| 2011/0020877 A1 | 1/2011 | Clark et al. |
| 2011/0104761 A1 | 5/2011 | Clark et al. |

FOREIGN PATENT DOCUMENTS

| | | |
|---|---|---|
| EP | 0 745 675 A2 | 12/1996 |
| EP | 1 757 698 A1 | 2/2007 |
| WO | 92/06188 A2 | 4/1992 |
| WO | 92/06200 A1 | 4/1992 |
| WO | 96/10640 A1 | 4/1996 |
| WO | 01/92501 A1 | 12/2001 |
| WO | 03/046149 A2 | 6/2003 |
| WO | WO 03/048308 | 6/2003 |
| WO | 2004/037979 A2 | 5/2004 |
| WO | 2005/118815 A1 | 12/2005 |
| WO | WO 2006/030455 | 3/2006 |
| WO | 2006/074233 A2 | 7/2006 |
| WO | 2007/011891 A2 | 1/2007 |
| WO | 2007/043769 A1 | 4/2007 |
| WO | WO 2007/127893 | 11/2007 |
| WO | 2009/087394 A1 | 7/2009 |
| WO | WO 2009/087394 | 7/2009 |
| WO | 2009/112867 A1 | 9/2009 |
| WO | 2009/112868 A1 | 9/2009 |

OTHER PUBLICATIONS

Mincer et al. Genbank Accession No. ABK80648, Nov. 2007.*
Ngo et al. In the Protein Folding Problem and Tertiary Structure Prediction, 1994, Merz et al. (ed.), Birkhauser, Boston, MA, pp. 433 and 492-495.*
Mincer, et al. (2007) *Environ Microbiol.* 9(5): 1162-75 [ABSTRACT].
Guo et al., "Biochemical and Structural Characterization of Cren7, a Novel Chromatin Protein Conserved Among Crenarchaea," Nucleic Acids Research, vol. 36, No. 4, pp. 1129-1137 (2008) XP-002526277.
Moussard et al., "Thermodesulfatator Indics gen. nov., sp. nov., a novel Thermophilic Chemolithoautotrophic Sulfate-Reducing Bacterium Isolated from the Central Indian Ridge," International Journal of Systematic and Evolutionary Microbiology, vol. 54, pp. 227-233 (2004) XP-002526275.
Notomi et al., "Loop-Mediated Isothermal Amplification of DNA," Nucleic Acids Research, vol. 28, No. 12, (2000).
Southworth et al., Cloning of Thermostable DNA Polymerases from Hyperthermophilic Marine Archaea with Emphasis on *Thermococcus* sp. 9°N-7 and Mutations Affecting 3'-5' Exonuclease Activity, Proc. Natl. Acad. Sci., vol. 93, pp. 5281-5285, May 1996 XP 000652319.
International Search Report for International Application No. PCT/GB2009/000411 mailed May 8, 2009.
Written Opinion for International Application No. PCT/GB2009/000411, mailed May 8, 2009.
United Kingdom Patent Office Search Report for Priority Application No. GB0803628.7, mailed Jun. 30, 2008.
Bowie, et al. (1991) "A Method to Identify Protein Sequences that Fold into a Known Three-Dimensional Structure." *Science* 253(5016): 164-170.
Chothia & Lesk (1986) "The relation between the divergence of sequence and structure in proteins." *The EMBO Journal* 5(4): 823-826.

(Continued)

*Primary Examiner* — Richard Hutson

(57) ABSTRACT

There is provided a polypeptide having thermostable DNA polymerase activity and comprising or consisting of an amino acid sequence with at least 55% identity to *Thermodesulfatator indicus* DNA polymerase I Large fragment shown in SEQ ID NO: 1 or in SEQ ID NO:32.

15 Claims, 5 Drawing Sheets

(56) References Cited

OTHER PUBLICATIONS

Derbyshire, et al. (1995) *Methods in Enzymology* 262: 363-385.
Hamilton, et al. (2001) *Biotechniques* 31: 370-383.
Ho, et al. (1989) "Site-directed mutagenesis by overlap extension using the polymerase chain reaction." *Gene* 77(1): 51-59 [Abstract].
Landt, et al. (1990) "A general method for rapid site-directed mutagenesis using the polymerase chain reaction." *Gene* 96(1): 125-128 [Abstract].
Nixon, et al. (1998) *TIBTECH* 16: 258-263.
Pavlov, et al. (2004) *Trends in Biotechnology* 22: 245-260.
Taylor (1988) "Pattern matching methods in protein sequence comparison and structure prediction." *Protein Engineering* 2(2): 77-86.
Villbrandt, et al. (2000) *Protein Engineering* 13: 645-654.
Voet & Voet *Biochemistry* (1990), Chapter 8 "Protein Folding, Dynamics, and Structural Evolution" pp. 193-244.
Amend et al., "*Palaeococcus helgesonii* Sp. Nov., a Facultatively Anaerobic, Hyperthermophilic Archaeon from a Geothermal Well on Vulcano Island, Italy," Archives of Microbiology, 2003, pp. 394-401, vol. 179.
American Heritage Science Dictionary, entry for "stop codon" (2002).
Barnes, "The fidelity of Taq polymerase catalyzing PCR is improved by an N-terminal deletion," Gene, 1992, pp. 29-35, vol. 112.
Chaparro-Riggers et al., "Better library design: data-driven protein engineering," J. Biotechnol., 2007, pp. 180-191 [Abstract], vol. 2, No. 2.
Database Geneseq [Online] retrieved from Accession No. AEE85221, XP002534619 (2006).
Database Geneseq [Online] retrieved from EBI Accession No. GSP: AEE85205, XP002534728 (2006).
Database Geneseq [Online] retrieved from EBI Accession No. GSP: AFS77634, XP002534727 (2007).
Database UniProt [Online] retrieved from EMBL EBI Accession No. UniProt: A0SXL5, XP002534623 (2007).
Database UniProt [Online] retrieved from EMBL EBI Accession No. UniProt: Q2Q453, XP002534622 (2006).
Database UniProt [Online] XP002519040, Database Accession No. B1YCQ5, May 20, 2008.
Database UniProt [Online] XP002519041, Database Accession No. A8MCT2, Jul. 22, 2008.
Database UniProt [Online] XP002519042, Database Accession No. P00836, Jul. 22, 2008.
Davidson et al., "Insertion of the T3 DNA polymerase thioredoxin binding domain enhances the processivity and fidelity of Taq DNA polymerase," Nucleic Acids Research, 2003, pp. 4702-4709, vol. 31, No. 16.
DeLange et al., "A Histone-like Protein (HTa) from *Thermoplasma acidophilum*," The Journal of Biological Chemistry, 1981, pp. 900-904, vol. 256, No. 2.
Engelke et al., "Purification of *Thermus aquaticus* DNA Polymerase Expressed in *Escherichia coli*," Analytical Biochemistry, 1990, pp. 396-400, vol. 191.
Final Office Action from related U.S. Appl. No. 12/922,384, dated Jan. 2, 2013, 10 pgs.
Final Office Action from related U.S. Appl. No. 12/922,401, dated Jan. 11, 2013, 12 pgs.
Final Office Action from related U.S. Appl. No. 12/812,519, dated Mar. 11, 2013, 13 pgs.
Flaman et al., "A rapid PCR fidelity assay," Nucleic Acids Research, 1994, pp. 3259-3260, vol. 22, No. 15.
Forterre et al., "Identification of the gene encoding archeal-specific DNA-binding proteins of the Sac10b family," Molecular Microbiology, 1999, pp. 669-670, vol. 32, No. 3.
Griffiths et al., "New high fidelity polymerases from *Thermococcus* species," Protein Expression and Purification, 2007, pp. 19-30, vol. 52.
Hardy et al., "Biochemical characterization of DNA-binding proteins from *Pyrobaculum aerophilum* and *Aeropyrum pernix*," Extremophiles, 2008, pp. 235-246, vol. 12, No. 2.
Hodges et al., GenBank Accession No. AAA72101.1, Aug. 1993.

ISR and Written Opinion for International Application No. PCT/GB2009/000063, mailed Mar. 25, 2009, 17 pgs.
ISR and Written Opinion for International Application No. PCT/GB2009/050246, mailed Jul. 13, 2009, 12 pgs.
ISR and Written Opinion for International Application No. PCT/GB2009/050247, mailed Jul. 15, 2009, 11 pgs.
Ito et al., "Compilation and alignment of DNA polymerase sequences," Nucleic Acids Research, 1991, pp. 4045-4057, vol. 19, No. 15.
Joyce & Steitz, "Function and Structure Relationships in DNA Polymerases," Annu. Rev. Biochem., 1994, pp. 777-822, vol. 63.
Kim et al., "Cloning, Purification, and Characterization of a New DNA Polymerase from a Hyperthermophilic Archaeon, *Thermococcus* sp. NA1," J. Microbiol. Biotechnol., 2007, pp. 1090-1097, vol. 17, No. 7.
Lawyer et al., "High-level Expression, Purification, and Enzymatic Characterization of Full-length *Thermus aquaticus* DNA Polymerase and a Truncated Form Deficient in 5' to 3' Exonuclease Activity," PCR Methods and Applications, 1993, pp. 275-287, vol. 2.
Le Cam et al., "DNA Bending Induced by the Archaebacterial Histone-like Protein MC1," Journal of Molecular Biology, 1999, pp. 1011-1021, vol. 285, No. 3.
Lu et al., "Expression in *Escherichia coli* of the Thermostable DNA Polymerase from *Pyrococcus furiosus*," Protein Expression and Purification, 1997, pp. 179-184, vol. 11.
Lundberg et al., "High-fidelity amplification using a thermostable DNA polymerase isolated from *Pyrococcus furiosus*," Gene, 1991, pp. 1-6, vol. 108.
Luo et al., "CC1, a Novel Crenarchaeal DNA Binding Protein," Journal of Bacteriology, 2007, pp. 403-409, vol. 189, No. 2.
Motz et al., "Elucidation of an Archaeal Replication Protein Network to Generate Enchanced PCR Enzymes*," The Journal of Biological Chemistry, 2002, pp. 16179-16188, vol. 277, No. 18.
Non-Final Office Action from related U.S. Appl. No. 12/922,401, dated Aug. 7, 2012, 10 pgs.
Non-Final Office Action from related U.S. Appl. No. 12/922,384, dated Aug. 20, 2012, 12 pgs.
Non-Final Office Action from related U.S. Appl. No. 12/812,519, dated Oct. 26, 2012, 14 pgs.
Pavlov et al., "Helix-hairpin-helix motifs confer salt resistance and processivity on chimeric DNA polymerases," PNAS, 2002, pp. 13510-13515, vol. 99, No. 21.
Reeve, "Archaeal chromatin and transcription," Molecular Microbiology, 2003, pp. 587-598, vol. 48, No. 3.
Stark, "Multicopy expression vectors carrying the lac repressor gene for regulated high-level expression of genes in *Escherichia coli*," Gene, 1987, pp. 255-267, vol. 51.
Studier et al., "Use of T7 RNA Polymerase to Direct Expression of Cloned Genes," Methods in Enzymology, 1990, pp. 60-89, vol. 185.
Takagi et al., "Characterization of DNA Polymerase from *Pyrococcus* sp. Strain KOD1 and Its Application to PCR," Applied and Environmental Microbiology, 1997, pp. 4504-4510, vol. 63, No. 11.
Takai et al., "*Palaeococcus ferrophilus* gen. nov., a Barophilic, Hyperthermophilic Archaeon from a Deep-Sea Hydrothermal Vent Chimney," International Journal of Systematic and Evolutionary Microbiology, 2000, pp. 489-500, vol. 50, XP002534638.
Voet & Voet, Biochemistry [3rd Ed.] 2004, Table 30-2.
UK Search Report for Application No. GB0804722.7, mailed Jul. 11, 2008, 3 pgs.
UK Search Report for Application No. GB0804721.9, mailed Jul. 14, 2008, 4 pgs.
Wang et al., "A novel strategy to engineer DNA polymerases for enhanced processivity and improved performance in vitro," Nucleic Acids Research, 2004, pp. 1197-1207, vol. 32, No. 3.
Zhang et al., "Structural insights into the interaction of the crenarchaeal chromatin protein Cren7 with DNA", Molecular Microbiology, 2010, pp. 749-759, vol. 76, No. 3.
Altschul et al., "Basic Local Alignment Search Tool," J. Mol. Biol., 1990, pp. 403-410, vol. 215.
Brautigam and Steitz, "Structural and functional insights provided by crystal structures of DNA polymerases and their substrate complexes," Curr. Opin. Struct. Biol., 1998, pp. 54-63, vol. 8.

(56) References Cited

OTHER PUBLICATIONS

Campanella et al., "MatGAT: An application that generates similarity/identity matrices using protein or DNA sequences," BMC Bioinformatics, 2003, 4 pgs., vol. 4.

Delarue et al., "An attempt to unify the structure of polymerases," Protein Engineering, 1990, pp. 461-467, vol. 3, No. 6.

Gotz et al., "*Persephonella marina* gen. nov., sp. nov. and *Persephonella guaymasensis* sp. nov., two novel, thermophilic, hydrogen-oxidizing microaerophiles from deep-sea hydrothermal vents," Int. J. Syst. Evol. Microbiol., 2002, pp. 1349-1359, vol. 52.

Kunkel et al., "Exonucleolytic proofreading by calf thymus DNA polymerase o," PNAS, 1987, pp. 4865-4869, vol. 84.

Needleman and Wunsch, "A General Method Applicable to the Search for Similarities in the Amino Acid Sequence of Two Proteins," J. Mol. Biol., 1970, pp. 443-453, vol. 48.

Patel et al., "Prokaryotic DNA Polymerase I: Evolution, Structure, and "Base Flipping" Mechanism for Nucleotide Selection," J. Mol. Biol, 2001, pp. 823-837, vol. 308.

Shandilya et al., "Thermophilic bacterial DNA polymerases with reverse-transcriptase activity," Extremophiles, 2004, pp. 243-253, vol. 8.

Office Action from related U.S. Appl. No. 12/922,384, dated Oct. 30, 2014, 10 pgs.

Office Action from related U.S. Appl. No. 12/922,384, dated Jul. 15, 2014, 6 pgs.

Office Action from related U.S. Appl. No. 12/812,519, dated Aug. 20, 2014, 13 pgs.

Office Action from related U.S. Appl. No. 12/922,401, dated Nov. 4, 2014, 9 pgs.

Office Action from related U.S. Appl. No. 12/922,401, dated Jul. 24, 2014, 6 pgs.

\* cited by examiner

New pET24a(+)HIS region:

*Xba* I                                                                                                          *Nde* I
..tctaga aataattttgtttaactttaagaaggagatatactATGcaccatcaccatcaccatatggcta..
(SEQ ID NO:36)

M H H H H H H M
                                                            (SEQ ID NO:37)

SEQUENCE LISTING

```
<160> NUMBER OF SEQ ID NOS: 37

<210> SEQ ID NO 1
<211> LENGTH: 612
<212> TYPE: PRT
<213> ORGANISM: Thermodesulfatator indicus

<400> SEQUENCE: 1

Met Gly Leu Leu Lys Glu Leu Pro Ala Thr Lys Thr Leu Ser Met Thr
1               5                   10                  15

Arg Tyr Glu Leu Val Leu Asp Pro Asp Lys Val Lys Glu Ile Val Glu
                20                  25                  30

Lys Ala Lys Gly Ala Glu Val Val Ala Ile Asp Leu Glu Ser Asp Thr
            35                  40                  45

Lys Asp Pro Met Arg Gly Lys Ile Val Gly Val Ser Leu Cys Phe Asn
        50                  55                  60

Pro Pro Lys Ala Tyr Tyr Phe Pro Phe Arg His Gly Leu Glu Ala
65                  70                  75                  80

Gln Lys Gln Leu Pro Trp Glu Ala Phe Thr His Leu Ala Ser Leu Ile
                85                  90                  95

Glu Asp Pro Ser Val Lys Lys Ile Gly His Asn Ile Lys Tyr Asp Leu
                100                 105                 110

Ile Ile Leu Ala Arg Tyr Gly Val Thr Leu Lys Gly Leu Glu Gly Asp
            115                 120                 125

Thr Met Leu Ala Ser Tyr Leu Leu Asp Pro Thr Arg Arg Thr His Gly
        130                 135                 140

Leu Asp Glu Leu Ala Glu Glu Val Leu Gly His Thr Met Ile Phe Tyr
145                 150                 155                 160

Lys Glu Val Thr Lys Glu Leu Ala Lys Gly Glu Ser Phe Ala Arg Val
                165                 170                 175

Pro Leu Glu Lys Ala Lys Val Tyr Ala Cys Glu Asp Ala His Val Thr
                180                 185                 190

Tyr Leu Leu Tyr Gln Tyr Phe Trp Pro Lys Leu Lys Glu Glu Ser Leu
            195                 200                 205

Trp Lys Val Phe Thr Glu Ile Asp Arg Pro Leu Ile Glu Val Leu Ala
        210                 215                 220

His Met Glu Met Val Gly Ile Lys Ile Asp Thr Ala Tyr Leu Arg Gly
225                 230                 235                 240

Leu Ser Arg Glu Met Ala Glu Lys Leu Lys Glu Leu Glu Lys Ile
                245                 250                 255

Tyr Thr Leu Ala Gly Glu Lys Phe Asn Ile Asn Ser Ser Lys Gln Leu
                260                 265                 270

Gly Gln Ile Leu Phe Glu Lys Leu Lys Leu Pro Thr Val Lys Lys Thr
            275                 280                 285

Pro Lys Lys Thr Ala Tyr Ser Thr Asp Asn Glu Val Leu Glu Glu Leu
        290                 295                 300
```

Ser Ala Val His Glu Leu Pro Arg Leu Ile Leu Glu Tyr Arg Thr Leu
305                 310                 315                 320

Ala Lys Leu Lys Ser Thr Tyr Val Asp Ala Leu Pro Lys Met Val Asn
            325                 330                 335

Pro Glu Thr Gly Arg Leu His Thr Ser Phe Asn Gln Thr Val Thr Ala
        340                 345                 350

Thr Gly Arg Leu Ser Ser Asp Pro Asn Leu Gln Asn Ile Pro Val
    355                 360                 365

Arg Gly Glu Glu Gly Leu Lys Ile Arg Gln Ala Phe Val Pro Glu Glu
370                 375                 380

Ile Phe Ala Ala Asp Tyr Thr Gln Ile Asp Leu Arg Val Leu Ala His
385                 390                 395                 400

Tyr Ser Gly Asp Glu Thr Leu Ile Lys Ala Phe Trp Gln Gly Glu Asp
                405                 410                 415

Ile His Arg Arg Thr Ala Ala Glu Ile Phe Gly Ile Pro Pro Glu Glu
            420                 425                 430

Val Thr Pro Glu Met Arg Arg Met Ala Lys Thr Ile Asn Phe Gly Ile
        435                 440                 445

Val Tyr Gly Met Ser Pro Tyr Gly Leu Ala Lys Glu Leu Lys Ile Gly
    450                 455                 460

Arg Arg Glu Ala Lys Ala Phe Ile Glu Arg Tyr Phe Glu Arg Tyr Pro
465                 470                 475                 480

Gly Val Lys Arg Tyr Met Glu Gln Ile Val Ala Glu Ala Arg Glu Lys
                485                 490                 495

Gly Tyr Val Glu Thr Leu Phe Gly Arg Lys Arg Pro Leu Pro Asp Ile
            500                 505                 510

Asn Ser Pro Asn Arg Thr Ala Arg Glu Phe Ala Glu Arg Thr Ala Ile
        515                 520                 525

Asn Thr Pro Ile Gln Gly Thr Ala Ala Asp Ile Ile Lys Leu Ala Met
    530                 535                 540

Ile Lys Ile His Arg Ile Phe Lys Glu Lys Gly Phe Gly Thr Arg Met
545                 550                 555                 560

Leu Leu Gln Val His Asp Glu Leu Ile Phe Glu Ala Pro Lys Glu Ile
                565                 570                 575

Glu Glu Ile Gln Pro Ile Val Arg Gln Ile Met Glu Gly Val Val Glu
            580                 585                 590

Leu Lys Val Pro Leu Lys Val Asn Leu Ala Ile Gly Lys Asn Trp Ala
        595                 600                 605

Glu Ala Lys Ala
    610

<210> SEQ ID NO 2
<211> LENGTH: 900
<212> TYPE: PRT
<213> ORGANISM: Thermodesulfatator indicus

<400> SEQUENCE: 2

Met Ala Gln Lys Ser Leu Phe Pro Lys Lys Leu Pro Phe Lys Asp Asp
1               5                   10                  15

Lys Asp Pro Ile Phe Val Ile Asp Gly Ser Ser Phe Val Tyr Arg Ala
            20                  25                  30

Tyr Tyr Ala Ile Arg Gly His Leu Ser Asn Arg Lys Gly Leu Pro Thr
        35                  40                  45

Lys Ala Val Phe Gly Phe Thr Gln Met Leu Leu Lys Leu Leu Arg Glu

```
              50                  55                  60
Met Asn Pro Glu Tyr Val Val Cys Phe Asp Ala Lys Gly Pro Thr
 65                  70                  75                  80

Phe Arg His Glu Met Tyr Lys Glu Tyr Lys Ala Asn Arg Pro Pro Met
                     85                  90                  95

Pro Asp Asp Leu Ser Val Gln Ile Pro Tyr Ile Lys Glu Val Thr Arg
                    100                 105                 110

Ala Phe Gly Val Pro Ile Leu Glu Ile Glu Gly Phe Glu Ala Asp Asp
                115                 120                 125

Leu Ile Ala Ala Ile Ala Thr Arg Met Glu Arg Pro Ile Val Ile Val
130                 135                 140

Gly Gly Asp Lys Asp Leu Phe Pro Leu Ile Ser Glu Lys Val Val Met
145                 150                 155                 160

Trp Asp Pro Met Lys Asp Glu Leu Ile Asp Glu Ser Trp Ile Lys Lys
                165                 170                 175

Arg Phe Gly Ile Glu Pro Lys Lys Leu Leu Asp Val Arg Ala Leu Ala
                180                 185                 190

Gly Asp Ser Ile Asp Asn Val Pro Gly Val Pro Gly Ile Gly Glu Lys
                195                 200                 205

Thr Ala Leu Arg Leu Ile Lys Glu Tyr Gly Ser Leu Glu Glu Val Leu
210                 215                 220

Asn His Ala Glu Glu Ile Lys Gln Lys Arg Leu Arg Glu Asn Leu Ile
225                 230                 235                 240

Lys His Ala Gly Asp Ala Leu Ile Ser Lys Lys Leu Val Glu Leu Glu
                245                 250                 255

Ala Lys Ala Pro Ile Pro Leu Glu Pro Asp Phe Tyr Arg Lys Arg Pro
                260                 265                 270

Leu Asn Ala Leu Lys Leu Arg Glu Leu Phe Leu Glu Leu Glu Phe Lys
                275                 280                 285

Lys Leu Leu Lys Glu Leu Pro Ala Thr Lys Thr Leu Ser Met Thr Arg
                290                 295                 300

Tyr Glu Leu Val Leu Asp Pro Asp Lys Val Lys Glu Ile Val Glu Lys
305                 310                 315                 320

Ala Lys Gly Ala Glu Val Ala Ile Asp Leu Glu Ser Asp Thr Lys
                325                 330                 335

Asp Pro Met Arg Gly Lys Ile Val Gly Val Ser Leu Cys Phe Asn Pro
                340                 345                 350

Pro Lys Ala Tyr Tyr Phe Pro Phe Arg His Glu Gly Leu Glu Ala Gln
                355                 360                 365

Lys Gln Leu Pro Trp Glu Ala Phe Thr His Leu Ala Ser Leu Ile Glu
                370                 375                 380

Asp Pro Ser Val Lys Lys Ile Gly His Asn Ile Lys Tyr Asp Leu Ile
385                 390                 395                 400

Ile Leu Ala Arg Tyr Gly Val Thr Leu Lys Gly Leu Glu Gly Asp Thr
                    405                 410                 415

Met Leu Ala Ser Tyr Leu Leu Asp Pro Thr Arg Arg Thr His Gly Leu
                420                 425                 430

Asp Glu Leu Ala Glu Glu Val Leu Gly His Thr Met Ile Phe Tyr Lys
                435                 440                 445

Glu Val Thr Lys Glu Leu Ala Lys Gly Glu Ser Phe Ala Arg Val Pro
                450                 455                 460

Leu Glu Lys Ala Lys Val Tyr Ala Cys Glu Asp Ala His Val Thr Tyr
465                 470                 475                 480
```

```
Leu Leu Tyr Gln Tyr Phe Trp Pro Lys Leu Lys Glu Ser Leu Trp
            485                 490                 495

Lys Val Phe Thr Glu Ile Asp Arg Pro Leu Ile Glu Val Leu Ala His
            500                 505                 510

Met Glu Met Val Gly Ile Lys Ile Asp Thr Ala Tyr Leu Arg Gly Leu
            515                 520                 525

Ser Arg Glu Met Ala Glu Lys Leu Lys Glu Leu Glu Glu Lys Ile Tyr
530                 535                 540

Thr Leu Ala Gly Glu Lys Phe Asn Ile Asn Ser Ser Lys Gln Leu Gly
545                 550                 555                 560

Gln Ile Leu Phe Glu Lys Leu Lys Leu Pro Thr Val Lys Thr Pro
            565                 570                 575

Lys Lys Thr Ala Tyr Ser Thr Asp Asn Glu Val Leu Glu Glu Leu Ser
            580                 585                 590

Ala Val His Glu Leu Pro Arg Leu Ile Leu Glu Tyr Arg Thr Leu Ala
            595                 600                 605

Lys Leu Lys Ser Thr Tyr Val Asp Ala Leu Pro Lys Met Val Asn Pro
            610                 615                 620

Glu Thr Gly Arg Leu His Thr Ser Phe Asn Gln Thr Val Thr Ala Thr
625                 630                 635                 640

Gly Arg Leu Ser Ser Ser Asp Pro Asn Leu Gln Asn Ile Pro Val Arg
                    645                 650                 655

Gly Glu Glu Gly Leu Lys Ile Arg Gln Ala Phe Val Pro Glu Glu Ile
                    660                 665                 670

Phe Ala Ala Asp Tyr Thr Gln Ile Asp Leu Arg Val Leu Ala His Tyr
            675                 680                 685

Ser Gly Asp Glu Thr Leu Ile Lys Ala Phe Trp Gln Gly Glu Asp Ile
            690                 695                 700

His Arg Arg Thr Ala Ala Glu Ile Phe Gly Ile Pro Pro Glu Val
705                 710                 715                 720

Thr Pro Glu Met Arg Arg Met Ala Lys Thr Ile Asn Phe Gly Ile Val
                    725                 730                 735

Tyr Gly Met Ser Pro Tyr Gly Leu Ala Lys Glu Leu Lys Ile Gly Arg
            740                 745                 750

Arg Glu Ala Lys Ala Phe Ile Glu Arg Tyr Phe Glu Arg Tyr Pro Gly
            755                 760                 765

Val Lys Arg Tyr Met Glu Gln Ile Val Ala Glu Ala Arg Glu Lys Gly
            770                 775                 780

Tyr Val Glu Thr Leu Phe Gly Arg Lys Arg Pro Leu Pro Asp Ile Asn
785                 790                 795                 800

Ser Pro Asn Arg Thr Ala Arg Glu Phe Ala Glu Arg Thr Ala Ile Asn
                    805                 810                 815

Thr Pro Ile Gln Gly Thr Ala Ala Asp Ile Ile Lys Leu Ala Met Ile
                    820                 825                 830

Lys Ile His Arg Ile Phe Lys Glu Lys Gly Phe Gly Thr Arg Met Leu
            835                 840                 845

Leu Gln Val His Asp Glu Leu Ile Phe Glu Ala Pro Glu Lys Glu Ile
            850                 855                 860

Glu Glu Ile Gln Pro Ile Val Arg Gln Ile Met Glu Gly Val Val Glu
865                 870                 875                 880

Leu Lys Val Pro Leu Lys Val Asn Leu Ala Ile Gly Lys Asn Trp Ala
                    885                 890                 895
```

Glu Ala Lys Ala
         900

<210> SEQ ID NO 3
<211> LENGTH: 1839
<212> TYPE: DNA
<213> ORGANISM: Thermodesulfatator indicus

<400> SEQUENCE: 3

| | | | | | |
|---|---|---|---|---|---:|
| atgggcctct | taaaggaact | tccagctact | aaaacccttt | cgatgaccag | atacgagctg | 60 |
| gttcttgacc | cggataaagt | aaaagaaatt | gtagaaaagg | ccaaggggc | cgaagtggtg | 120 |
| gctattgacc | ttgaaagtga | tacgaaagac | cccatgcgtg | ggaaaatagt | agggtctcg | 180 |
| ctttgtttta | acccgcccaa | agcctattat | ttcccttttta | gacatgaagg | ccttgaggcc | 240 |
| caaaagcagc | ttccctggga | ggcctttact | catctggcca | gcctcattga | agaccccctca | 300 |
| gttaaaaaga | taggccacaa | tatcaagtat | gacttgatta | ttcttgctcg | ctacggcgta | 360 |
| actttaaagg | gccttgaagg | ggataccatg | ctggcttcgt | atctccttga | tccaacacgt | 420 |
| cgtacccacg | gccttgatga | gctggccgaa | gaggtcctgg | ggcataccat | gatttttttac | 480 |
| aaggaagtga | ctaaagaact | ggccaaagga | gagagctttg | ccagggtccc | tcttgaaaag | 540 |
| gcaaaagttt | acgcctgtga | agacgcccac | gttacctatc | tgctttatca | atatttctgg | 600 |
| cccaaactca | agaggaaag | cctctggaag | gtctttacgg | aaattgatcg | acctttaata | 660 |
| gaagttttgg | cccacatgga | aatggtaggt | attaagattg | acaccgccta | tcttagagga | 720 |
| cttttcgcgag | aaatggctga | aaagttaaag | gagcttgaag | aaaaaattta | caccctggct | 780 |
| ggtgaaaaat | ttaatatcaa | ttccagcaaa | caactgggcc | agattttatt | tgaaaagcta | 840 |
| aaactcccta | cggttaaaaa | gaccccaaaa | aaacggcct | attcaacgga | taacgaagta | 900 |
| ttagaggaac | tttctgcggt | ccacgaactt | ccgcgtctga | tacttgagta | tagaactctg | 960 |
| gctaaactca | aatctactta | tgttgatgcc | ctcccgaaga | tggttaatcc | tgaaactggt | 1020 |
| cgtcttcata | cttcctttaa | ccagacggtt | acggccactg | gaagactttc | aagcagtgac | 1080 |
| cctaatcttc | aaaatattcc | tgtgcgtggt | gaagagggc | ttaagattcg | ccaggccttt | 1140 |
| gtgccggagg | agattttttgc | tgccgattac | actcagatcg | atctgcgagt | tttagcccat | 1200 |
| tactcgggag | atgaaacctt | gattaaggcc | ttctggcagg | gggaagacat | tcaccggcgc | 1260 |
| acggctgcaa | aaattttttgg | tatcccgcca | gaagaagtaa | ctcctgagat | gcggcgtatg | 1320 |
| gccaagacta | taaactttgg | cattgtttac | ggcatgagtc | cttacggtct | ggcgaaagaa | 1380 |
| ctcaaaattg | gccgccgtga | ggccaaggcc | tttattgagc | gctatttga | acgctaccca | 1440 |
| ggtgtgaaac | gctatatgga | acaaatcgtg | gctgaagccc | gagaaaaggg | ctacgtggag | 1500 |
| acccttttcg | gacgcaaaag | gcctcttcct | gacatcaata | gccctaatcg | tacggcgcgc | 1560 |
| gagtttgccg | agcgcacggc | tataaacact | cctattcagg | ggacagccgc | tgatattatc | 1620 |
| aagctcgcca | tgataaaaat | tcaccggatt | ttttaaagaaa | aaggctttgg | gacaaggatg | 1680 |
| cttcttcagg | tgcatgacga | gcttattttt | gaagcgccaa | aagagattga | agaaatccag | 1740 |
| ccaattgtcc | gacaaatcat | ggaaggagtg | gttgaattga | aggttcctct | aaaagtaaac | 1800 |
| ctggcaatag | ggaaaaattg | ggcagaggca | aaggcataa | | | 1839 |

<210> SEQ ID NO 4
<211> LENGTH: 2703
<212> TYPE: DNA
<213> ORGANISM: Thermodesulfatator indicus

```
<400> SEQUENCE: 4
atggcgcaga aaagcttgtt tcctaaaaaa ttaccattta aagatgataa agacccatc      60 ttcgttattg acgggagttc ttttgtttac cgggcttact atgccataag agggcatcta    120
tcaaaccgca aagggctccc aaccaaggcg gtctttgggt ttacccagat gcttttaaag    180
cttttgcgtg agatgaaccc tgagtatgtg gtggtgtgct ttgacgccaa agggcctact    240
tttcgccacg agatgtacaa agaatacaaa gccaaccgcc ccccatgcc  agatgatctt    300 tccgtccaga ttccctatat caagagggta accagggcct tggagtccc  tattcttgaa    360 atagaaggct ttgaagctga cgatctcatc gccgctattg ccactcgtat ggaaagacca    420
attgtcatcg ttggtggaga taaagatttg ttcccccctta tttcagagaa agttgtcatg    480
tgggacccca tgaaagacga actgattgac gaaagctgga taagaaacg  ttttggcatt    540 gaacctaaaa agctccttga tgtaagggcc cttgccggcg atagcattga taacgtgcca    600
ggggttccgg gtattggtga aaaaacggcc ctaaggctca taaaagaata cggttccctt    660
gaagaagtcc ttaaccatgc cgaagaaata aaacaaaagc gcttgcgtga aaacctcatc    720
aaacacgccg agacgccct  tatttccaaa aaactggttg agcttgaggc caaagcccca    780 atccccctt  agcctgattt ttaccgcaaa cggccattaa atgccctaaa actaagggaa    840
ctcttccttg agcttgaatt taaaaagctc ttaaaggaac ttccagctac taaaaccctt    900
tcgatgacca gatacgagct ggttcttgac ccggataaag taaaagaaat tgtagaaaag    960
gccaaggggg ccgaagtggt ggctattgac cttgaaagtg tacgaaaga  ccccatgcgt   1020 gggaaaatag tagggggtctc gctttgttt  aacccgccca agcctatta  ttccccttt   1080 agacatgaag gccttgaggc ccaaaagcag cttccctggg aggcctttac tcatctggcc   1140
agcctcattg aagaccctc  agttaaaaag ataggccaca atatcaagta tgacttgatt   1200
attcttgctc gctacggcgt aactttaaag ggccttgaag gggataccat gctggcttcg   1260
tatctccttg atccaacacg tcgtacccac ggccttgatg agctggccga agaggtcctg   1320
gggcatacca tgatttttta caaggaagtg actaagaac  tggccaaagg agagagcttt   1380
gccagggtcc ctcttgaaaa ggcaaaagtt tacgcctgtg aagacgccca cgttacctat   1440
ctgctttatc aatatttctg gcccaaactc aaagaggaaa gcctctggaa ggtctttacg   1500
gaaattgatc gaccttttaat agaagttttg gcccacatgg aaatggtagg tattaagatt   1560
gacaccgcct atcttagagg actttcgcga gaaatggctg aaaagttaaa ggagcttgaa   1620 gaaaaattt  acaccctggc tggtgaaaaa tttaatatca attccagcaa caactgggc    1680 cagattttat ttgaaaagct aaaactccct acggttaaaa agaccccaaa aaaaacggcc   1740
tattcaacgg ataacgaagt attagaggaa cttctctgcgg tccacgaact tccgcgtctg   1800
atacttgagt atagaactct ggctaaactc aaatctactt atgttgatgc cctcccgaag   1860
atggttaatc ctgaaactgg tcgtcttcat acttccttta accagacggt tacggccact   1920
ggaagacttt caagcagtga ccctaatctt caaaatattc ctgtgcgtgg tgaagagggg   1980
cttaagattc gccaggcctt tgtgccggag gagattttg  ctgccgatta cactcagatc   2040
gatctgcgag ttttagccca ttactcggga gatgaaacct tgattaaggc cttctggcag   2100
ggggaagaca ttcaccggcg cacggctgca gaaattttg  gtatcccgcc agaagaagta   2160
actcctgaga tgcggcgtat ggccaagact ataaactttg gcattgttta cggcatgagt   2220
ccttacggtc tggcgaaaga actcaaaatt ggccgccgtg aggccaaggc ctttattgag   2280
cgctattttg aacgctaccc aggtgtgaaa cgctatatgg aacaaatcgt ggctgaagcc   2340
```

```
cgagaaaagg gctacgtgga gacccttttc ggacgcaaaa ggcctcttcc tgacatcaat    2400
agccctaatc gtacggcgcg cgagtttgcc gagcgcacgg ctataaacac tcctattcag    2460
gggacagccg ctgatattat caagctcgcc atgataaaaa ttcaccggat ttttaaagaa    2520
aaaggctttg ggacaaggat gcttcttcag gtgcatgacg agcttatttt tgaagcgcct    2580
gaaaaagaga ttgaagaaat ccagccaatt gtccgacaaa tcatggaagg agtggttgaa    2640
ttgaaggttc tctaaaagt aaacctggca atagggaaaa attgggcaga ggcaaaggca     2700
taa                                                                  2703
```

```
<210> SEQ ID NO 5
<211> LENGTH: 30
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (22)..(22)
<223> OTHER INFORMATION: n is a, c, g, or t

<400> SEQUENCE: 5 cattttttgct gccgattayw sncarathga                                    30

<210> SEQ ID NO 6
<211> LENGTH: 28
<212> TYPE: DNA
<213> ORGANISM: Artificial Sequence
<220> FEATURE:
<223> OTHER INFORMATION: Primer sequence

<400> SEQUENCE: 6
aaccgcgaag tttttattyr agyagyac                                       28

<210> SEQ ID NO 7
<211> LENGTH: 18
<212> TYPE: DNA
<213> ORGANISM: Artificial Sequence
<220> FEATURE:
<223> OTHER INFORMATION: Primer sequence

<400> SEQUENCE: 7
tgtaaaacga cggccagt                                                  18

<210> SEQ ID NO 8
<211> LENGTH: 24
<212> TYPE: DNA
<213> ORGANISM: Artificial Sequence
<220> FEATURE:
<223> OTHER INFORMATION: Primer sequence

<400> SEQUENCE: 8
agcggataac aatttcacac agga                                           24

<210> SEQ ID NO 9
<211> LENGTH: 20
<212> TYPE: DNA
<213> ORGANISM: Artificial Sequence
<220> FEATURE:
<223> OTHER INFORMATION: Primer sequence

<400> SEQUENCE: 9
aatcaaggtt tcatctcccg                                                20
```

```
<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10
tattcagggg acagccgctg                                                  20

<210> SEQ ID NO 11
<211> LENGTH: 20
<212> TYPE: DNA
<213> ORGANISM: Artificial Sequence
<220> FEATURE:
<223> OTHER INFORMATION: Primer sequence

<400> SEQUENCE: 11
taatgggcta aaactcgcag                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer sequence

<400> SEQUENCE: 12
aaggctttgg gacaaggatg                                                  20

<210> SEQ ID NO 13
<211> LENGTH: 19
<212> TYPE: DNA
<213> ORGANISM: Artificial Sequence
<220> FEATURE:
<223> OTHER INFORMATION: Primer sequence

<400> SEQUENCE: 13
tctcgctttg ttttaaccc                                                   19

<210> SEQ ID NO 14
<211> LENGTH: 19
<212> TYPE: DNA
<213> ORGANISM: Artificial Sequence
<220> FEATURE:
<223> OTHER INFORMATION: Primer sequence

<400> SEQUENCE: 14
catgcgtggg aaaatagta                                                   19

<210> SEQ ID NO 15
<211> LENGTH: 20
<212> TYPE: DNA
<213> ORGANISM: Artificial Sequence
<220> FEATURE:
<223> OTHER INFORMATION: Primer sequence

<400> SEQUENCE: 15
actttatccg ggtcaagaac                                                  20

<210> SEQ ID NO 16
<211> LENGTH: 21
<212> TYPE: DNA
<213> ORGANISM: Artificial Sequence
<220> FEATURE:
<223> OTHER INFORMATION: Primer sequence
```

```
<400> SEQUENCE: 16
tttcgtatca ctttcaaggt c                                              21

<210> SEQ ID NO 17
<211> LENGTH: 56
<212> TYPE: DNA
<213> ORGANISM: Artificial Sequence
<220> FEATURE:
<223> OTHER INFORMATION: Primer sequence

<400> SEQUENCE: 17
gtccaccata tggcgcagaa aagcttgttt cctaaaaaat taccatttaa agatga       56

<210> SEQ ID NO 18
<211> LENGTH: 38
<212> TYPE: DNA
<213> ORGANISM: Artificial Sequence
<220> FEATURE:
<223> OTHER INFORMATION: Primer sequence

<400> SEQUENCE: 18
cttgaacata tgggcctctt aaaagaactt ccagctac                            38

<210> SEQ ID NO 19
<211> LENGTH: 42
<212> TYPE: DNA
<213> ORGANISM: Artificial Sequence
<220> FEATURE:
<223> OTHER INFORMATION: Primer sequence

<400> SEQUENCE: 19
agccctgtcg acggatccgc cagcttatgc ctttgcctct gc                       42

<210> SEQ ID NO 20
<211> LENGTH: 55
<212> TYPE: DNA
<213> ORGANISM: Artificial Sequence
<220> FEATURE:
<223> OTHER INFORMATION: Primer sequence

<400> SEQUENCE: 20
ttcccctcta gaaataattt tgtttaactt taagaaggag atatactatg cacca         55

<210> SEQ ID NO 21
<211> LENGTH: 55
<212> TYPE: DNA
<213> ORGANISM: Artificial Sequence
<220> FEATURE:
<223> OTHER INFORMATION: Primer sequence

<400> SEQUENCE: 21
gaattcggat ccgctagcca tatggtgatg gtgatggtgc atagtatatc tcctt         55

<210> SEQ ID NO 22
<211> LENGTH: 24
<212> TYPE: DNA
<213> ORGANISM: Artificial Sequence
<220> FEATURE:
<223> OTHER INFORMATION: Primer sequence

<400> SEQUENCE: 22
aaattaatac gactcactat aggg                                           24

<210> SEQ ID NO 23
```

```
<211> LENGTH: 19
<212> TYPE: DNA
<213> ORGANISM: Artificial Sequence
<220> FEATURE:
<223> OTHER INFORMATION: Primer sequence

<400> SEQUENCE: 23
gctagttatt gctcagcgg                                                    19

<210> SEQ ID NO 24
<211> LENGTH: 25
<212> TYPE: DNA
<213> ORGANISM: Artificial Sequence
<220> FEATURE:
<223> OTHER INFORMATION: Primer sequence

<400> SEQUENCE: 24
gatgagttcg tgtccgtaca actgg                                             25

<210> SEQ ID NO 25
<211> LENGTH: 25
<212> TYPE: DNA
<213> ORGANISM: Artificial Sequence
<220> FEATURE:
<223> OTHER INFORMATION: Primer sequence

<400> SEQUENCE: 25
ggttatcgaa atcagccaca gcgcc                                             25

<210> SEQ ID NO 26
<211> LENGTH: 46
<212> TYPE: DNA
<213> ORGANISM: Artificial Sequence
<220> FEATURE:
<223> OTHER INFORMATION: Primer sequence

<400> SEQUENCE: 26
cagccagccg cagcacgttc gctcatagga gatatggtag agccgc                      46

<210> SEQ ID NO 27
<211> LENGTH: 51
<212> TYPE: DNA
<213> ORGANISM: Artificial Sequence
<220> FEATURE:
<223> OTHER INFORMATION: Primer sequence

<400> SEQUENCE: 27
gagagaattt gtaccacctc ccaccgggca catagcagtc ctagggacag t                51

<210> SEQ ID NO 28
<211> LENGTH: 22
<212> TYPE: DNA
<213> ORGANISM: Artificial Sequence
<220> FEATURE:
<223> OTHER INFORMATION: Primer sequence

<400> SEQUENCE: 28
ggcttggctc tgctaacacg tt                                                22

<210> SEQ ID NO 29
<211> LENGTH: 22
<212> TYPE: DNA
<213> ORGANISM: Artificial Sequence
<220> FEATURE:
<223> OTHER INFORMATION: Primer sequence

<400> SEQUENCE: 29
```

-continued

```
ggacgtttgt aatgtccgct cc                                              22

<210> SEQ ID NO 30
<211> LENGTH: 17
<212> TYPE: DNA
<213> ORGANISM: Artificial Sequence
<220> FEATURE:
<223> OTHER INFORMATION: Primer sequence

<400> SEQUENCE: 30
ctgcatacga cgtgtct                                                    17

<210> SEQ ID NO 31
<211> LENGTH: 20
<212> TYPE: DNA
<213> ORGANISM: Artificial Sequence
<220> FEATURE:
<223> OTHER INFORMATION: Primer sequence

<400> SEQUENCE: 31
accatctatg actgtacgcc                                                 20

<210> SEQ ID NO 32
<211> LENGTH: 613
<212> TYPE: PRT
<213> ORGANISM: Thermodesulfatator indicus

<400> SEQUENCE: 32

Met Gly Leu Leu Lys Glu Leu Pro Ala Thr Lys Thr Leu Ser Tyr Asp
1               5                   10                  15

Gln Tyr Glu Leu Val Leu Asp Pro Asp Lys Val Lys Glu Ile Val Glu
            20                  25                  30

Lys Ala Lys Gly Ala Glu Val Val Ala Ile Asp Leu Glu Ser Asp Thr
        35                  40                  45

Lys Asp Pro Met Arg Gly Lys Ile Val Gly Val Ser Leu Cys Phe Asn
    50                  55                  60

Pro Pro Lys Ala Tyr Tyr Phe Pro Phe Arg His Glu Gly Leu Glu Ala
65                  70                  75                  80

Gln Lys Gln Leu Pro Trp Glu Ala Phe Thr His Leu Ala Ser Leu Ile
                85                  90                  95

Glu Asp Pro Ser Val Lys Lys Ile Gly His Asn Ile Lys Tyr Asp Leu
            100                 105                 110

Ile Ile Leu Ala Arg Tyr Gly Val Thr Leu Lys Gly Leu Glu Gly Asp
        115                 120                 125

Thr Met Leu Ala Ser Tyr Leu Leu Asp Pro Thr Arg Arg Thr His Gly
    130                 135                 140

Leu Asp Glu Leu Ala Glu Glu Val Leu Gly His Thr Met Ile Phe Tyr
145                 150                 155                 160

Lys Glu Val Thr Lys Glu Leu Ala Lys Gly Glu Ser Phe Ala Arg Val
                165                 170                 175

Pro Leu Glu Lys Ala Lys Val Tyr Ala Cys Glu Asp Ala His Val Thr
            180                 185                 190

Tyr Leu Leu Tyr Gln Tyr Phe Trp Pro Lys Leu Lys Glu Glu Ser Leu
        195                 200                 205

Trp Lys Val Phe Thr Glu Ile Asp Arg Pro Leu Ile Glu Val Leu Ala
    210                 215                 220

His Met Glu Met Val Gly Ile Lys Ile Asp Thr Ala Tyr Leu Arg Gly
225                 230                 235                 240
```

```
Leu Ser Arg Glu Met Ala Glu Lys Leu Lys Glu Leu Glu Glu Lys Ile
            245                 250                 255

Tyr Thr Leu Ala Gly Glu Lys Phe Asn Ile Asn Ser Ser Lys Gln Leu
        260                 265                 270

Gly Gln Ile Leu Phe Glu Lys Leu Lys Leu Pro Thr Val Lys Lys Thr
    275                 280                 285

Pro Lys Lys Thr Ala Tyr Ser Thr Asp Asn Glu Val Leu Glu Glu Leu
290                 295                 300

Ser Ala Val His Glu Leu Pro Arg Leu Ile Leu Glu Tyr Arg Thr Leu
305                 310                 315                 320

Ala Lys Leu Lys Ser Thr Tyr Val Asp Ala Leu Pro Lys Met Val Asn
                325                 330                 335

Pro Glu Thr Gly Arg Leu His Thr Ser Phe Asn Gln Thr Val Thr Ala
            340                 345                 350

Thr Gly Arg Leu Ser Ser Ser Asp Pro Asn Leu Gln Asn Ile Pro Val
        355                 360                 365

Arg Gly Glu Glu Gly Leu Lys Ile Arg Gln Ala Phe Val Pro Glu Glu
370                 375                 380

Ile Phe Ala Ala Asp Tyr Thr Gln Ile Asp Leu Arg Val Leu Ala His
385                 390                 395                 400

Tyr Ser Gly Asp Glu Thr Leu Ile Lys Ala Phe Trp Gln Gly Glu Asp
                405                 410                 415

Ile His Arg Arg Thr Ala Ala Glu Ile Phe Gly Ile Pro Pro Glu Glu
            420                 425                 430

Val Thr Pro Glu Met Arg Arg Met Ala Lys Thr Ile Asn Phe Gly Ile
        435                 440                 445

Val Tyr Gly Met Ser Pro Tyr Gly Leu Ala Lys Glu Leu Lys Ile Gly
    450                 455                 460

Arg Arg Glu Ala Lys Ala Phe Ile Glu Arg Tyr Phe Glu Arg Tyr Pro
465                 470                 475                 480

Gly Val Lys Arg Tyr Met Glu Gln Ile Val Ala Glu Ala Arg Glu Lys
                485                 490                 495

Gly Tyr Val Glu Thr Leu Phe Gly Arg Lys Arg Pro Leu Pro Asp Ile
            500                 505                 510

Asn Ser Pro Asn Arg Thr Ala Arg Glu Phe Ala Glu Arg Thr Ala Ile
        515                 520                 525

Asn Thr Pro Ile Gln Gly Thr Ala Ala Asp Ile Ile Lys Leu Ala Met
    530                 535                 540

Ile Lys Ile His Arg Ile Phe Lys Glu Lys Gly Phe Gly Thr Arg Met
545                 550                 555                 560

Leu Leu Gln Val His Asp Glu Leu Leu Phe Glu Val Pro Glu Lys Glu
                565                 570                 575

Ile Glu Glu Ile Gln Pro Ile Val Arg Gln Ile Met Glu Gly Val Val
            580                 585                 590

Glu Leu Lys Val Pro Leu Lys Val Asn Leu Ala Ile Gly Lys Asn Trp
        595                 600                 605

Ala Glu Ala Lys Ala
    610
```

<210> SEQ ID NO 33
<211> LENGTH: 1842
<212> TYPE: DNA
<213> ORGANISM: Thermodesulfatator indicus

<400> SEQUENCE: 33

```
atgggcctct taaaggaact tccagctact aaaacccttt cgtatgacca gtacgagctg      60
gttcttgacc cggataaagt aaaagaaatt gtagaaaagg ccaaggggc cgaagtggtg      120
gctattgacc ttgaaagtga tacgaaagac cccatgcgtg gaaaatagt aggggtctcg     180
ctttgtttta acccgcccaa agcctattat ttccttttta gacatgaagg ccttgaggcc    240
caaaagcagc ttccctggga ggcctttact catctggcca gcctcattga agaccccctca   300
gttaaaaga taggccacaa tatcaagtat gacttgatta ttcttgctcg ctacggcgta     360
actttaaagg gccttgaagg ggataccatg ctggcttcgt atctccttga tccaacacgt   420
cgtacccacg gccttgatga gctggccgaa gaggtcctgg ggcataccat gattttttac  480
aaggaagtga ctaaagaact ggccaaagga gagagctttg ccagggtccc tcttgaaaag  540
gcaaaagttt acgcctgtga agacgcccac gttacctatc tgctttatca atatttctgg  600
cccaaactca aagaggaaag cctctggaag gtctttacgg aaattgatcg accttttaata 660
gaagttttgg cccacatgga aatggtaggt attaagatta caccgcctat cttagagga   720
ctttcgcgag aaatggctga aaagttaaag gagcttgaag aaaaaatta caccctggct   780
ggtgaaaaat ttaatatcaa ttccagcaaa caactgggcc agattttatt tgaaaagcta 840
aaactcccta cggttaaaaa gaccccaaaa aaacggcct attcaacgga taacgaagta  900
ttagaggaac tttctgcggt ccacgaactt ccgcgtctga tacttgagta tagaactctg  960
gctaaactca aatctactta tgttgatgcc ctcccgaaga tggttaatcc tgaaactggt 1020
cgtcttcata cttcctttaa ccagacggtt acggccactg aaagactttc aagcagtgac 1080
cctaatcttc aaaatattcc tgtgcgtggt gaagaggggc ttaagattcg ccaggccttt 1140
gtgccggagg agattttgc tgccgattac actcagatcg atctgcgagt tttagcccat 1200
tactcgggag atgaaacctt gattaaggcc ttctggcagg gggaagacat tcaccggcgc 1260
acggctgcag aaatttttgg tatcccgcca gaagaagtaa ctcctgagat gcggcgtatg 1320
gccaagacta taaactttgg cattgtttac ggcatgagtc cttacggtct ggcgaaagaa 1380
ctcaaaattg gccgccgtga ggccaaggcc tttattgagc gctattttga acgctaccca 1440
ggtgtgaaac gctatatgga acaaatcgtg gctgaagccc gagaaaaggg ctacgtggag 1500
acccttttcg gacgcaaaag gcctcttcct gacatcaata gccctaatcg tacggcgcgc 1560
gagtttgccg agcgcacggc tataaacact cctattcagg ggacagccgc tgatattatc 1620
aagctcgcca tgataaaaat tcaccggatt tttaaagaaa aaggctttgg gacaaggatg 1680
cttcttcagg tgcacgacga acttcttttt gaagtgcctg aaaaagagat tgaagaaatc 1740
cagccaattg tccgacaaat catggaagga gtggttgaat tgaaggttcc tctaaaagta 1800
aacctggcaa taggaaaaaa ttgggcagag gcaaaggcat aa                     1842
```

<210> SEQ ID NO 34
<211> LENGTH: 900
<212> TYPE: PRT
<213> ORGANISM: Thermodesulfatator indicus

<400> SEQUENCE: 34

```
Met Ala Gln Lys Ser Leu Phe Pro Lys Lys Leu Pro Phe Lys Asp Asp
1               5                   10                  15

Lys Asp Pro Ile Phe Val Ile Asp Gly Ser Ser Phe Val Tyr Arg Ala
            20                  25                  30

Tyr Tyr Ala Ile Arg Gly His Leu Ser Asn Arg Lys Gly Leu Pro Thr
```

```
                35                  40                  45
Lys Ala Val Phe Gly Phe Thr Gln Met Leu Leu Lys Leu Leu Arg Glu
 50                  55                  60

Met Asn Pro Glu Tyr Val Val Cys Phe Asp Ala Lys Gly Pro Thr
 65                  70                  75                  80

Phe Arg His Glu Met Tyr Lys Glu Tyr Lys Ala Asn Arg Pro Pro Met
                 85                  90                  95

Pro Asp Asp Leu Ser Val Gln Ile Pro Tyr Ile Lys Glu Val Thr Arg
                100                 105                 110

Ala Phe Gly Val Pro Ile Leu Glu Ile Glu Gly Phe Glu Ala Asp Asp
                115                 120                 125

Leu Ile Ala Ala Ile Ala Thr Arg Met Glu Arg Pro Ile Val Ile Val
                130                 135                 140

Gly Gly Asp Lys Asp Leu Phe Pro Leu Ile Ser Glu Lys Val Val Met
145                 150                 155                 160

Trp Asp Pro Met Lys Asp Glu Leu Ile Asp Glu Ser Trp Ile Lys Lys
                165                 170                 175

Arg Phe Gly Ile Glu Pro Lys Lys Leu Leu Asp Val Arg Ala Leu Ala
                180                 185                 190

Gly Asp Ser Ile Asp Asn Val Pro Gly Val Pro Gly Ile Gly Glu Lys
                195                 200                 205

Thr Ala Leu Arg Leu Ile Lys Glu Tyr Gly Ser Leu Glu Glu Val Leu
                210                 215                 220

Asn His Ala Glu Glu Ile Lys Gln Lys Arg Leu Arg Glu Asn Leu Ile
225                 230                 235                 240

Lys His Ala Gly Asp Ala Leu Ile Ser Lys Lys Leu Val Glu Leu Glu
                245                 250                 255

Ala Lys Ala Pro Ile Pro Leu Glu Pro Asp Phe Tyr Arg Lys Arg Pro
                260                 265                 270

Leu Asn Ala Leu Lys Leu Arg Glu Leu Phe Leu Glu Leu Glu Phe Lys
                275                 280                 285

Lys Leu Leu Lys Glu Leu Pro Ala Thr Lys Thr Leu Ser Tyr Asp Gln
                290                 295                 300

Tyr Glu Leu Val Leu Asp Pro Asp Lys Val Lys Glu Ile Val Glu Lys
305                 310                 315                 320

Ala Lys Gly Ala Glu Val Val Ala Ile Asp Leu Glu Ser Asp Thr Lys
                325                 330                 335

Asp Pro Met Arg Gly Lys Ile Val Gly Val Ser Leu Cys Phe Asn Pro
                340                 345                 350

Pro Lys Ala Tyr Tyr Phe Pro Phe Arg His Glu Gly Leu Glu Ala Gln
                355                 360                 365

Lys Gln Leu Pro Trp Glu Ala Phe Thr His Leu Ala Ser Leu Ile Glu
                370                 375                 380

Asp Pro Ser Val Lys Lys Ile Gly His Asn Ile Lys Tyr Asp Leu Ile
385                 390                 395                 400

Ile Leu Ala Arg Tyr Gly Val Thr Leu Lys Gly Leu Glu Gly Asp Thr
                405                 410                 415

Met Leu Ala Ser Tyr Leu Leu Asp Pro Thr Arg Arg Thr His Gly Leu
                420                 425                 430

Asp Glu Leu Ala Glu Glu Val Leu Gly His Thr Met Ile Phe Tyr Lys
                435                 440                 445

Glu Val Thr Lys Glu Leu Ala Lys Gly Glu Ser Phe Ala Arg Val Pro
                450                 455                 460
```

Leu Glu Lys Ala Lys Val Tyr Ala Cys Glu Asp Ala His Val Thr Tyr
465                 470                 475                 480

Leu Leu Tyr Gln Tyr Phe Trp Pro Lys Leu Lys Glu Glu Ser Leu Trp
            485                 490                 495

Lys Val Phe Thr Glu Ile Asp Arg Pro Leu Ile Glu Val Leu Ala His
            500                 505                 510

Met Glu Met Val Gly Ile Lys Ile Asp Thr Ala Tyr Leu Arg Gly Leu
            515                 520                 525

Ser Arg Glu Met Ala Glu Lys Leu Lys Glu Leu Glu Glu Lys Ile Tyr
            530                 535                 540

Thr Leu Ala Gly Glu Lys Phe Asn Ile Asn Ser Ser Lys Gln Leu Gly
545                 550                 555                 560

Gln Ile Leu Phe Glu Lys Leu Lys Leu Pro Thr Val Lys Lys Thr Pro
            565                 570                 575

Lys Lys Thr Ala Tyr Ser Thr Asp Asn Glu Val Leu Glu Glu Leu Ser
            580                 585                 590

Ala Val His Glu Leu Pro Arg Leu Ile Leu Glu Tyr Arg Thr Leu Ala
            595                 600                 605

Lys Leu Lys Ser Thr Tyr Val Asp Ala Leu Pro Lys Met Val Asn Pro
610                 615                 620

Glu Thr Gly Arg Leu His Thr Ser Phe Asn Gln Thr Val Thr Ala Thr
625                 630                 635                 640

Gly Arg Leu Ser Ser Ser Asp Pro Asn Leu Gln Asn Ile Pro Val Arg
            645                 650                 655

Gly Glu Glu Gly Leu Lys Ile Arg Gln Ala Phe Val Pro Glu Glu Ile
            660                 665                 670

Phe Ala Ala Asp Tyr Thr Gln Ile Asp Leu Arg Val Leu Ala His Tyr
            675                 680                 685

Ser Gly Asp Glu Thr Leu Ile Lys Ala Phe Trp Gln Gly Glu Asp Ile
            690                 695                 700

His Arg Arg Thr Ala Ala Glu Ile Phe Gly Ile Pro Pro Glu Glu Val
705                 710                 715                 720

Thr Pro Glu Met Arg Arg Met Ala Lys Thr Ile Asn Phe Gly Ile Val
            725                 730                 735

Tyr Gly Met Ser Pro Tyr Gly Leu Ala Lys Glu Leu Lys Ile Gly Arg
            740                 745                 750

Arg Glu Ala Lys Ala Phe Ile Glu Arg Tyr Phe Glu Arg Tyr Pro Gly
            755                 760                 765

Val Lys Arg Tyr Met Glu Gln Ile Val Ala Glu Ala Arg Glu Lys Gly
            770                 775                 780

Tyr Val Glu Thr Leu Phe Gly Arg Lys Arg Pro Leu Pro Asp Ile Asn
785                 790                 795                 800

Ser Pro Asn Arg Thr Ala Arg Glu Phe Ala Glu Arg Thr Ala Ile Asn
            805                 810                 815

Thr Pro Ile Gln Gly Thr Ala Ala Asp Ile Ile Lys Leu Ala Met Ile
            820                 825                 830

Lys Ile His Arg Ile Phe Lys Glu Lys Gly Phe Gly Thr Arg Met Leu
            835                 840                 845

Leu Gln Val His Asp Glu Leu Leu Phe Glu Val Pro Glu Lys Glu Ile
            850                 855                 860

Glu Glu Ile Gln Pro Ile Val Arg Gln Ile Met Glu Gly Val Val Glu
865                 870                 875                 880

Leu Lys Val Pro Leu Lys Val Asn Leu Ala Ile Gly Lys Asn Trp Ala
            885                 890                 895

Glu Ala Lys Ala
            900

<210> SEQ ID NO 35
<211> LENGTH: 2703
<212> TYPE: DNA
<213> ORGANISM: Thermodesulfatator indicus

<400> SEQUENCE: 35

| | | | | | |
|---|---|---|---|---|---|
| atggcgcaga | aaagcttgtt | tcctaaaaaa | ttaccattta | aagatgataa | agaccccatc | 60 |
| ttcgttattg | acgggagttc | ttttgtttac | cgggcttact | atgccataag | agggcatcta | 120 |
| tcaaaccgca | aagggctccc | aaccaaggcg | gtctttgggt | ttacccagat | gcttttaaag | 180 |
| cttttgcgtg | agatgaaccc | tgagtatgtg | gtggtgtgct | tgacgccaa | agggcctact | 240 |
| tttcgccacg | agatgtacaa | agaatacaaa | gccaaccgcc | ccccatgcc | agatgatctt | 300 |
| tccgtccaga | ttccctatat | caagaggta | accaggcct | tggagtccc | tattcttgaa | 360 |
| atagaaggct | tgaagctga | cgatctcatc | gccgctattg | ccactcgtat | ggaaagacca | 420 |
| attgtcatcg | ttggtggaga | taaagatttg | ttccccctta | tttcagagaa | agttgtcatg | 480 |
| tgggaccca | tgaaagacga | actgattgac | gaaagctgga | taaagaaacg | ttttggcatt | 540 |
| gaacctaaaa | agctccttga | tgtaagggc | cttgccggcg | atagcattga | taacgtgcca | 600 |
| ggggttccgg | gtattggtga | aaaacggcc | ctaaggctca | taaaagaata | cggttccctt | 660 |
| gaagaagtcc | ttaaccatgc | cgaagaaata | aaacaaaagc | gcttgcgtga | aaacctcatc | 720 |
| aaacacgccg | agacgccct | tatttccaaa | aaactggttg | agcttgaggc | caaagcccca | 780 |
| atccccttg | agcctgattt | taccgcaaa | cggccattaa | atgccctaaa | actaagggaa | 840 |
| ctcttccttg | agcttgaatt | taaaaagctc | ttaaggaac | ttccagctac | taaaacccctt | 900 |
| tcgtatgacc | agtacgagct | ggttcttgac | ccggataaag | taaagaaat | tgtagaaaag | 960 |
| gccaaagggg | ccgaagtggt | ggctattgac | cttgaaagtg | atacgaaaga | ccccatgcgt | 1020 |
| gggaaaatag | taggggtctc | gcttttgttt | aacccgccca | aagcctatta | tttcccttt | 1080 |
| agacatgaag | gccttgaggc | ccaaaagcag | cttccctggg | aggcctttac | tcatctggcc | 1140 |
| agcctcattg | aagacccctc | agttaaaaag | ataggccaca | atatcaagta | tgacttgatt | 1200 |
| attcttgctc | gctacggcgt | aactttaaag | ggccttgaag | gggataccat | gctggcttcg | 1260 |
| tatctccttg | atccaacacg | tcgtaccac | ggccttgatg | agctggccga | agaggtcctg | 1320 |
| gggcatacca | tgattttta | caaggaagtg | actaagaac | tggccaaagg | agagagcttt | 1380 |
| gccagggtcc | ctcttgaaaa | ggcaaaagtt | tacgcctgtg | aagacgccca | cgttacctat | 1440 |
| ctgctttatc | aatatttctg | gcccaaactc | aaagaggaaa | gcctctggaa | ggtctttacg | 1500 |
| gaaattgatc | gacctttaat | agaagttttg | gcccacatgg | aaatggtagg | tattaagatt | 1560 |
| gacaccgcct | atcttagagg | actttcgcga | gaaatggctg | aaaagttaaa | ggagcttgaa | 1620 |
| gaaaaatttt | acaccctggc | tggtgaaaaa | tttaatatca | attccagcaa | caactgggc | 1680 |
| cagattttat | ttgaaaagct | aaaactccct | acggttaaaa | agacccccaaa | aaaaacggcc | 1740 |
| tattcaacgg | ataacgaagt | attagaggaa | ctttctgcgg | tccacgaact | tccgcgtctg | 1800 |
| atacttgagt | atagaactct | ggctaaactc | aaatctactt | atgttgatgc | cctcccgaag | 1860 |
| atggttaatc | ctgaaactgg | tcgtcttcat | acttcctta | accagacggt | tacggccact | 1920 |
| ggaagacttt | caagcagtga | ccctaatctt | caaaatattc | ctgtgcgtgg | tgaagagggg | 1980 |

-continued

```
cttaagattc gccaggcctt tgtgccggag gagattttg ctgccgatta cactcagatc    2040
gatctgcgag ttttagccca ttactcggga gatgaaacct tgattaaggc cttctggcag    2100
ggggaagaca ttcaccggcg cacggctgca gaattttg gtatcccgcc agaagaagta    2160
actcctgaga tgcggcgtat ggccaagact ataaactttg gcattgttta cggcatgagt    2220
ccttacggtc tggcgaaaga actcaaaatt ggccgccgtg aggccaaggc ctttattgag    2280
cgctattttg aacgctaccc aggtgtgaaa cgctatatgg aacaaatcgt ggctgaagcc    2340
cgagaaaagg gctacgtgga gaccctttc ggacgcaaaa ggcctcttcc tgacatcaat    2400
agccctaatc gtacggcgcg cgagtttgcc gagcgcacgg ctataaacac tcctattcag    2460
gggacagccg ctgatattat caagctcgcc atgataaaaa ttcaccggat ttttaaagaa    2520
aaaggctttg gacaaggat gcttcttcag gtgcacgacg aacttctttt tgaagtgcct    2580 gaaaagaga ttgaagaaat ccagccaatt gtccgacaaa tcatggaagg agtggttgaa    2640
ttgaaggttc ctctaaaagt aaacctggca atagggaaaa attgggcaga ggcaaaggca    2700
taa                                                                  2703
```

<210> SEQ ID NO 36
<211> LENGTH: 69
<212> TYPE: DNA
<213> ORGANISM: Artificial Sequence
<220> FEATURE:
<223> OTHER INFORMATION: Plasmid fragment

<400> SEQUENCE: 36

```
tctagaaata attttgttta actttaagaa ggagatatac tatgcaccat caccatcacc    60
atatggcta                                                            69
```

<210> SEQ ID NO 37
<211> LENGTH: 8
<212> TYPE: PRT
<213> ORGANISM: Artificial Sequence
<220> FEATURE:
<223> OTHER INFORMATION: Protein tag sequence

<400> SEQUENCE: 37

```
Met His His His His His His Met
1               5
```

THERMOSTABLE DNA POLYMERASE

CROSS REFERENCE TO RELATED APPLICATIONS

This application is the National Phase application of International Application No. PCT/GB2009/000411, filed Feb. 13, 2009, which claims the benefit of priority to GB Patent Application No. 0803628.7, filed Feb. 28, 2008, the disclosures of each of which are herein incorporated by reference in their entireties.

FIELD OF INVENTION

The present invention relates to novel polypeptides having DNA polymerase activity, and their uses.

BACKGROUND

DNA polymerases are enzymes involved in vivo in DNA repair and replication, but have become an important in vitro diagnostic and analytical tool for the molecular biologist. *E. coli* DNA polymerase I encoded by the gene "DNA polA" was discovered in 1956, and cloned and characterised in the early 1970s. The enzyme has a variety of uses including DNA labelling by nick translation, second-strand cDNA synthesis in cDNA cloning, and DNA sequencing. The so-called "Klenow" or "Large" fragment of *E. coli* DNA polymerase I is a large protein fragment originally produced upon cleavage of the native enzyme by the protease enzyme subtilisin. This Large fragment exhibits 5'→3' polymerase activity and 3'→5' exonuclease proofreading activity, but loses 5'→3' exonuclease activity which mediates nick translation during DNA repair in the native enzyme.

Since being discovered in *E. coli*, DNA polymerase I-like enzymes have been characterised in many prokaryotes, although the non-*E. coli* counterparts do not always have a 3'→5' exonuclease proofreading function. Certain DNA polymerase I—like enzymes obtained from various thermophilic eubacteria, for example *Thermus flavus, Thermus aquaticus, Thermus brockianus, Thermus ruber, Thermus thermophilus, Thermus filiformis, Thermus lacteus, Thermus rubens, Bacillus stearothermophilus, Bacillus caldotenax* and *Thermotoga maritima*, have been found to be thermostable, retaining polymerase activity at around 45° C. to 100° C.

In general, thermostable DNA polymerases have found wide use in methods for amplifying nucleic acid sequences by thermocycling amplification reactions such as the polymerase chain reaction (PCR) or by isothermal amplification reactions such as strand displacement amplification (SDA), nucleic acid sequence-based amplification (NASBA), self-sustained sequence replication (3SR), and loop-mediated isothermal amplification (LAMP; see Notomi et al., 2000, Nucleic Acids Res. 28: e63). Thermostable DNA polymerases have different properties such as thermostability, strand displacement activity, fidelity (error rate) and binding affinity to template DNA and/or free nucleotides, and are therefore typically suited to different types of amplification reaction.

Isothermal amplification reactions require a DNA polymerase with strong strand displacement activity, and DNA polymerase I enzymes such as Bst DNA polymerase I Large fragment and Bca DNA polymerase I Large fragment are preferred in reactions such as LAMP (see Notomi et al., 2000, supra).

On the other hand, thermocycling amplification reactions such as PCR require a DNA polymerase with reasonable processivity and thermostability at the cycling temperatures used (typically up to 94° C.). Many of the commercially used DNA polymerases for PCR are DNA polymerase II-like enzymes (for example, Vent, Deep Vent, Pwo, Pfu, KOD, 9N7, Tfu DNA polymerases) which lack 5'→3' exonuclease activity but have proofreading 3'→5' exonuclease activity. Some DNA polymerase I enzymes (typically those from *Thermotoga* and *Thermus* species, for example Taq DNA polymerase) are used in PCR, but Taq DNA polymerase, for example, has insufficient strand displacement activity to function adequately in isothermal amplification reactions.

WO2007/127893 discloses thermostable DNA polymerases from *Thermotoga naphthophila* and *Thermotoga petrophellia*.

Moussard et al. (Int. J. Systemic & Evolutionary Microbiol. (2004) 54: 227-233) discloses the discovery of the genus *Thermodesulfatator*, with *Thermodesulfatator indicus* as the type species.

The present invention provides a novel thermostable DNA polymerase I and Large fragment thereof for use in reactions requiring DNA polymerase activity such as nucleic acid amplification reactions. The polymerase, particularly its Large fragment, has surprisingly and advantageously been found to be useful in both thermocycling and isothermal amplification reactions. Included within the scope of the present invention are various mutants (deletion and substitution) that retain thermostability and the ability to replicate DNA.

SUMMARY OF INVENTION

According to one aspect of the present invention there is provided a polypeptide having thermostable DNA polymerase activity and comprising or consisting essentially of an amino acid sequence with at least 51% identity, for example at least 55%, 56%, 57%, 58%, 59%, 60%, 65%, 70%, 75%, 80%, 85%, 90%, 91%, 92%, 93%, 94%, 95%, 96%, 97%, 98% or even 99% identity, to *Thermodesulfatator indicus* DNA polymerase I Large (or "Klenow") fragment shown in SEQ ID NO:1. Preferably, the polypeptide is isolated.

The Large fragment of *T. indicus* DNA polymerase I has the following amino acid sequence:

```
                                           (SEQ ID NO: 1)
MGLLKELPATKTLSMTRYELVLDPDKVKEIVEKAKGAEVVAIDLESDT

KDPMRGKIVGVSLCFNPPKAYYFPFRHEGLEAQKQLPWEAFTHLASLI

EDPSVKKIGHNIKYDLIILARYGVTLKGLEGDTMLASYLLDPTRRTHG

LDELAEEVLGHTMIFYKEVTKELAKGESFARVPLEKAKVYACEDAHVT

YLLYQYFWPKLKEESLWKVFTEIDRPLIEVLAHMEMVGIKIDTAYLRG

LSREMAEKLKELEEKIYTLAGEKFNINSSKQLGQILFEKLKLPTVKKT

PKKTAYSTDNEVLEELSAVHELPRLILEYRTLAKLKSTYVDALPKMVN

PETGRLHTSFNQTVTATGRLSSSDPNLQNIPVRGEEGLKIRQAFVPEE

IFAADYTQIDLRVLAHYSGDETLIKAFWQGEDIHRRTAAEIFGIPPEE

VTPEMRRMAKTINFGIVYGMSPYGLAKELKIGRREAKAFIERYFERYP

GVKRYMEQIVAEAREKGYVETLFGRKRPLPDINSPNRTAREFAERTAI

NTPIQGTAADIIKLAMIKIHRIFKEKGFGTRMLLQVHDELIFEAPKEI

EEIQPIVRQIMEGVVELKVPLKVNLAIGKNWAEAKA.
```

An alternative amino acid sequence, identified by further and improved sequencing analysis, for the Large fragment of *T. indicus* DNA polymerase I is SEQ ID NO:32 as follows:

(SEQ ID NO: 32)
MGLLKELPATKTLSYDQYELVLDPDKVKEIVEKAKGAEVVAIDLESDT

KDPMRGKIVGVSLCFNPPKAYYFPFRHEGLEAQKQLPWEAFTHLASLI

EDPSVKKIGHNIKYDLIILARYGVTLKGLEGDTMLASYLLDPTRRTHG

LDELAEEVLGHTMIFYKEVTKELAKGESFARVPLEKAKVYACEDAHVT

YLLYQYFWPKLKEESLWKVFTEIDRPLIEVLAHMEMVGIKIDTAYLRG

LSREMAEKLKELEEKIYTLAGEKFNINSSKQLGQILFEKLKLPTVKKT

PKKTAYSTDNEVLEELSAVHELPRLILEYRTLAKLKSTYVDALPKMVN

PETGRLHTSFNQTVTATGRLSSSDPNLQNIPVRGEEGLKIRQAFVPEE

IFAADYTQIDLRVLAHYSGDETLIKAFWQGEDIHRRTAAEIFGIPPEE

VTPEMRRMAKTINFGIVYGMSPYGLAKELKIGRREAKAFIERYFERYP

GVKRYMEQIVAEAREKGYVETLFGRKRPLPDINSPNRTAREFAERTAI

NTPIQGTAADIIKLAMIKIHRIFKEKGFGTRMLLQVHDELLFEVPEKE

IEEIQPIVRQIMEGVVELKVPLKVNLAIGKNWAEAKA

This sequence is 99% identical to SEQ ID NO:1.

The predicted molecular weight of the 613 amino acid residue *T. indicus* DNA polymerase I Large fragment shown in SEQ ID NO:32 is about 69,990 Daltons. The predicted molecular weight of the 612 amino acid residue sequence shown in SEQ ID NO:1 is about 69,820 Daltons.

The amino acid sequence for inclusion in the polypeptide according to the invention may be an amino acid sequence with at least 51% identity, for example at least 55%, 56%, 57%, 58%, 59%, 60%, 65%, 70%, 75%, 80%, 85%, 90%, 91%, 92%, 93%, 94%, 95%, 96%, 97%, 98% or even 99% identity, to the sequence shown in SEQ ID NO:32.

The percentage sequence identity may be determined using the BLASTP computer program with SEQ ID NO:1 or 32 as the base sequence. This means that SEQ ID NO:1 or 32, as appropriate, is the sequence against which the percentage identity is determined. The BLAST software is publicly available at http://blast.ncbi.nlm.nih.gov/Blast.cgi (accessible on 11 Feb. 2009).

*T. indicus* is a thermophilic chemolithoautotrophic sulphate-reducing bacterium isolated from a deep-sea hydrothermal vent site, and has a reported temperature range for growth of 55-80° C. and an optimum growth temperature of 70° C. (see Moussard et al., 2004, Int. J. Syst. Evol. Microbiol. 54: 227-233). The inventors have isolated genomic DNA (gDNA) from *T. indicus* and used a sophisticated gene walking technique to clone a DNA polymerase A (polA) gene encoding a DNA polymerase I and corresponding Large fragment thereof. The Large fragment having the amino acid sequence as shown in SEQ ID NO: 1 has been shown to be surprisingly efficient in both PCR and LAMP amplification reactions when compared with the different preferred DNA polymerases for these reactions. The ability of the *T. indicus* DNA polymerase I Large fragment to be sufficiently thermostable to function in PCR, with temperatures rising to around 94° C., could not have been predicted based on the optimum growth temperature of 70° C. for this bacterium.

The polypeptide of the invention may exhibit strand displacement activity. The polypeptide may accordingly be suitable for carrying out isothermal amplification reactions such as LAMP.

The polypeptide may additionally or alternatively be suitable for carrying out thermocycling amplification reactions such as PCR.

The polypeptide as described herein may be about 613 amino acid residues in length, for example from about 610 to about 620, about 600 to about 630, about 550 to about 650, or about 500 to about 750 amino acids in length.

The polypeptide may comprise or consist essentially of the amino acid sequence SEQ ID NO:1 or 32, or of the amino acid sequence of SEQ ID NO:1 or 32 with 1, 2, 3, 4, 5, 6, 7, 8, 9, 10, 11, 12, 13, 14, 15, about 20, about 30, about 40, about 50, about 100, about 200, about 250, about 260, about 270, 280, 281, 282, 283, 284, 285, 286, 287 or 288 contiguous amino acids added to or removed from any part of the polypeptide and/or 1, 2, 3, 4, 5, 6, 7, 8, 9, 10, 11, 12, 13, 14, 15, about 20, about 30, about 40, about 50, about 100, about 150, about 200, about 250, about 260, about 270, 280, 281, 282, 283, 284, 285, 286, 287 or 288 amino acids added to or removed from the N-terminus region and/or the C-terminus region.

In one embodiment where the polypeptide of the invention includes an N-terminal His tag, the full length may be 619 amino acid residues.

According to a further aspect of the invention, there is provided an isolated polypeptide having thermostable DNA polymerase activity and comprising or consisting essentially of an amino acid sequence with at least 55% identity, for example at least 55%, 60%, 65%, 70%, 75%, 80%, 85%, 90%, 95%, 96%, 97%, 98% or even 99% identity, to *T. indicus* DNA polymerase I as shown in SEQ ID NO:2.

Preferably, the polypeptide according to this aspect of the invention is a polypeptide according to the first aspect of the invention and, therefore, has at least 51% identity to *T. indicus* DNA polymerase I Large fragment shown in SEQ ID NO:1

*T. indicus* DNA polymerase I has a full length amino acid sequence as follows:

(SEQ ID NO: 2)
MAQKSLFPKKLPFKDDKDPIFVIDGSSFVYRAYYAIRGHLSNRKGLPT

KAVFGFTQMLLKLLREMNPEYVVVCFDAKGPTFRHEMYKEYKANRPPM

PDDLSVQIPYIKEVTRAFGVPILEIEGFEADDLIAAIATRMERPIVIV

GGDKDLFPLISEKVVMWDPMKDELIDESWIKKRFGIEPKKLLDVRALA

GDSIDNVPGVPGIGEKTALRLIKEYGSLEEVLNHAEEIKQKRLRENLI

KHAGDALISKKLVELEAKAPIPLEPDFYRKRPLNALKLRELFLELEFK

KLLKELPATKTLSMTRYELVLDPDKVKEIVEKAKGAEVVAIDLESDTK

DPMRGKIVGVSLCFNPPKAYYFPFRHEGLEAQKQLPWEAFTHLASLIE

DPSVKKIGHNIKYDLIILARYGVTLKGLEGDTMLASYLLDPTRRTHGL

DELAEEVLGHTMIFYKEVTKELAKGESFARVPLEKAKVYACEDAHVTY

LLYQYFWPKLKEESLWKVFTEIDRPLIEVLAHMEMVGIKIDTAYLRGL

SREMAEKLKELEEKIYTLAGEKFNINSSKQLGQILFEKLKLPTVKKTP

KKTAYSTDNEVLEELSAVHELPRLILEYRTLAKLKSTYVDALPKMVNP

ETGRLHTSFNQTVTATGRLSSSDPNLQNIPVRGEEGLKIRQAFVPEEI

FAADYTQIDLRVLAHYSGDETLIKAFWQGEDIHRRTAAEIFGIPPEEV

TPEMRRMAKTINFGIVYGMSPYGLAKELKIGRREAKAFIERYFERYPG

VKRYMEQIVAEAREKGYVETLFGRKRPLPDINSPNRTAREFAERTAIN

TPIQGTAADIIKLAMIKIHRIFKEKGFGTRMLLQVHDELIFEAPEKEI

EEIQPIVRQIMEGVVELKVPLKVNLAIGKNWAEAKA.

An alternative amino acid sequence, identified by further and improved sequencing analysis, for full length *T. indicus* DNA polymerase I is SEQ ID NO:34 as follows:

```
                                              (SEQ ID NO: 34)
MAQKSLFPKKLPFKDDKDPIFVIDGSSFVYRAYYAIRGHLSNRKGLPT

KAVFGFTQMLLKLLREMNPEYVVVCFDAKGPTFRHEMYKEYKANRPPM

PDDLSVQIPYIKEVTRAFGVPILEIEGFEADDLIAAIATRMERPIVIV

GGDKDLFPLISEKVVMWDPMKDELIDESWIKKRFGIEPKKLLDVRALA

GDSIDNVPGVPGIGEKTALRLIKEYGSLEEVLNHAEEIKQKRLRENLI

KHAGDALISKKLVELEAKAPIPLEPDFYRKRPLNALKLRELFLELEFK

KLLKELPATKTLSYDQYELVLDPDKVKEIVEKAKGAEVVAIDLESDTK

DPMRGKIVGVSLCFNPPKAYYFPFRHEGLEAQKQLPWEAFTHLASLIE

DPSVKKIGHNIKYDLIILARYGVTLKGLEGDTMLASYLLDPTRRTHGL

DELAEEVLGHTMIFYKEVTKELAKGESFARVPLEKAKVYACEDAHVTY

LLYQYFWPKLKEESLWKVFTEIDRPLIEVLAHMEMVGIKIDTAYLRGL

SREMAEKLKELEEKIYTLAGEKFNINSSKQLGQILFEKLKLPTVKKTP

KKTAYSTDNEVLEELSAVHELPRLILEYRTLAKLKSTYVDALPKMVNP

ETGRLHTSFNQTVTATGRLSSSDPNLQNIPVRGEEGLKIRQAFVPEEI

FAADYTQIDLRVLAHYSGDETLIKAFWQGEDIHRRTAAEIFGIPPEEV

TPEMRRMAKTINFGIVYGMSPYGLAKELKIGRREAKAFIERYFERYPG

VKRYMEQIVAEAREKGYVETLFGRKRPLPDINSPNRTAREFAERTAIN

TPIQGTAADIIKLAMIKIHRIFKEKGFGTRMLLQVHDELLFEVPEKEI

EEIQPIVRQIMEGVVELKVPLKVNLAIGKNWAEAKA
```

This sequence is 99.44% identical to SEQ ID NO:2.

The predicted molecular weight of this 900 amino acid residue *T. indicus* DNA polymerase I shown in SEQ ID NO:34 is about 102,900 Daltons. The predicted molecular weight of the 900 amino acid residue sequence shown in SEQ ID NO:2 is about 102,850 Daltons.

The amino acid sequence for inclusion in the polypeptide according to the invention may be an amino acid sequence with at least 51% identity, for example at least 52%, 53%, 54%, 55%, 56%, 57%, 58%, 59%, 60%, 65%, 70%, 75%, 80%, 85%, 90%, 91%, 92%, 93%, 94%, 95%, 96%, 97%, 98% or even 99% identity, to the sequence shown in SEQ ID NO:34.

The percentage sequence identity may be determined using the BLASTP computer program with SEQ ID NO:2 or 34 as the base sequence. This means that SEQ ID NO:2 or 34, as appropriate, is the sequence against which the percentage identity is determined.

The polypeptide may comprise or consist essentially of the amino acid sequence SEQ ID NO:2 or 34, or of the amino acid sequence of SEQ ID NO:2 or 34 with 1, 2, 3, 4, 5, 6, 7, 8, 9, 10, 11, 12, 13, 14, 15, about 20, about 30, about 40, about 50, about 100, about 150, about 200, about 250, about 260, about 270, 280, 281, 282, 283, 284, 285, 286, 287 or 288 contiguous amino acids added to or removed from any part of the polypeptide and/or 1, 2, 3, 4, 5, 6, 7, 8, 9, 10, 11, 12, 13, 14, 15, about 20, about 30, about 40, about 50, about 100, about 150, about 200, about 250, about 260, about 270, 280, 281, 282, 283, 284, 285, 286, 287 or 288 amino acids added to or removed from the N-terminus region and/or the C-terminus region.

The polypeptide according to this aspect of the invention may be an isolated thermostable DNA polymerase I obtainable from *T. indicus* and having a molecular weight of about 102,500 to 103,500 Daltons (preferably about 102,900 or about 103,000 Daltons), or an enzymatically active fragment thereof. The term "enzymatically active fragment" means a fragment of such a polymerase obtainable from *T. indicus* and having enzyme activity which is at least 60%, preferably at least 70%, more preferably at least 80%, yet more preferably 90%, 95%, 96%, 97%, 98%, 99% or 100% that of the full length polymerase being compared to. The given activity may be determined by any standard measure, for example, the number of bases of nucleotides of the template sequence which can be replicated in a given time period. The skilled person is routinely able to determine such properties and activities.

Residues 3-612 of the *T. indicus* DNA polymerase I Large fragment shown in SEQ ID NO: 1 correspond with residues 290-900 of the full length DNA polymerase I shown in SEQ ID NO:2. Residues 1-2 of SEQ ID NO:1 are artificially introduced compared to the sequence of SEQ ID NO:2 to allow in vitro expression of the Large fragment in a host cell (see Examples below). Similarly, residues 3-613 of the *T. indicus* DNA polymerase I Large fragment shown in SEQ ID NO: 32 correspond with residues 290-900 of the full length DNA polymerase I shown in SEQ ID NO:34.

The polypeptide according to the invention may be greater in size where, according to a further aspect of the invention, it comprises additional functional or structural domains, for example an affinity purification tag (such as an H is purification tag), or DNA polymerase activity-enhancing domains such as the proliferating cell nuclear antigen homologue from *Archaeoglobus fulgidus*, T3 DNA polymerase thioredoxin binding domain, DNA binding protein Sso7d from *Sulfolobus solfataricus*, Sso7d-like proteins, or mutants thereof, or helix-hairpin-helix motifs derived from DNA topoisomerase V. The DNA polymerase activity-enhancing domain may also be a Cren7 enhancer domain or variant thereof, as defined and exemplified in co-pending International patent application no. PCT/GB2009/000063, which discloses that this highly conserved protein domain from Crenarchaeal organisms is useful to enhance the properties of a DNA polymerase. International patent application no. PCT/GB2009/000063 is incorporated herein by reference in its entirety.

The polypeptides of the invention may be suitable for use in one or more reactions requiring DNA polymerase activity, for example one or more of the group consisting of: nick translation, second-strand cDNA synthesis in cDNA cloning, DNA sequencing, thermocycling amplification reactions such as PCR, and isothermal amplification reactions for example strand displacement amplification (SDA), nucleic acid sequence-based amplification (NASBA), self-sustained sequence replication (3SR) and LAMP.

Also provided according to the present invention is a polypeptide with thermostable 5'→3' exonuclease activity and having at least 55% identity, for example at least 55%, 60%, 65%, 70%, 75%, 80%, 85%, 90%, 95%, 96%, 97%, 98% or even 99% identity, to residues 1-289 of *T. indicus* DNA polymerase I as shown in SEQ ID NO: 2 or 34.

Based on sequence comparisons with known DNA polymerases, in one aspect the polypeptides of the invention have 3'→5' exonuclease proofreading activity.

In a further aspect of the invention the polypeptides exhibit high fidelity polymerase activity during a thermocycling amplification reaction (such as PCR). High fidelity may be defined as a PCR error rate of less than 1 nucleotide per $300 \times 10^6$ amplified nucleotides, for example less than 1 nucleotide per 250×10⁶, 200×10⁶, 150×10⁶, 100×10⁶ or 50×10⁶ amplified nucleotides. Alternatively, the error rate of the polypeptides may be in the range 1-300 nucleotides per 10⁶ amplified nucleotides, for example 1-200, 1-100, 100-300, 200-300, 100-200 or 75-200 nucleotides per 10⁶ amplified nucleotides. Error rate may be determined using the opal reversion assay as described by Kunkel et al. (1987, Proc. Natl. Acad. Sci. USA 84: 4865-4869).

In another aspect of the invention there is provided a composition comprising the polypeptide as described herein. The composition may for example include a buffer, most or all ingredients for performing a reaction (such as a DNA amplification reaction for example PCR or LAMP), a stabilizer (such as *E. coli* GroEL protein, to enhance thermostability), and/or other compounds.

The invention further provides an isolated nucleic acid encoding the polypeptide with identity to the *T. indicus* DNA polymerase I Large fragment. The nucleic acid may, for example, have a sequence as shown below (5'-3'):

```
                                          (SEQ ID NO: 3)
atgggcctcttaaaggaacttccagctactaaaacccttcgatgacc agatacgagctggttcttgacccggataaagtaaaagaaattgtagaa aaggccaaggggccgaagtggtggctattgaccttgaaagtgatacg aaagaccccatgcgtgggaaaatagtagggtctcgctttgttttaac ccgcccaaagcctattatttccttttagacatgaaggccttgaggcc caaaagcagcttccctggaggcctttactcatctggccagcctcatt gaagacccctcagttaaaagataggccacaatatcaagtatgacttg attattcttgctcgctacggcgtaactttaaagggccttgaaggggat accatgctggcttcgtatctccttgatccaacgtcgtacccacggc cttgatgagctggccgaagaggtcctggggcataccatgatttttac aaggaagtgactaaagaactggccaaaggagagagctttgccagggtc cctcttgaaaggcaaaagtttacgcctgtgaagacgcccacgttacc tatctgctttatcaatatttctggcccaaactcaaagaggaaagcctc tggaaggtctttacggaaattgatcgacctttaatagaagttttggcc
```

```
cacatggaaatggtaggtattaagattgacaccgcctatcttagagga ctttcgcgagaaatggctgaaaagttaaaggagcttgaagaaaaaatt tacaccctggctggtgaaaaatttaatatcaattccagcaaacaactg ggccagatttatttgaaaagctaaaactccctacggttaaaaagacc ccaaaaaaaacggcctattcaacggataacgaagtattagaggaactt tctgcggtccacgaacttccgcgtctgatacttgagtatagaactctg gctaaactcaaatctacttatgttgatgccctcccgaagatggttaat cctgaaactggtcgtcttcatacttcctttaaccagacggttacggcc actggaagactttcaagcagtgaccctaatcttcaaaatattcctgtg cgtggtgaagaggggcttaagattcgccaggcctttgtgccggaggag Atttttgctgccgattacactcagatcgatctgcgagttttagcccat tactcgggagatgaaaccttgattaaggccttctggcaggggaagac attcaccggcgcacggctgcagaaattttggtatcccgccagaagaa gtaactcctgagatgcggcgtatggccaagactataaacttggcatt gtttacggcatgagtccttacggtctggcgaaagaactcaaaattggc cgccgtgaggccaaggcctttattgagcgctattttgaacgctaccca ggtgtgaaacgctatatggaacaaatcgtggctgaagcccgagaaaag ggctacgtggagacccttttcggacgcaaaaggcctcttcctgacatc aatagccctaatcgtacggcgcgcgagtttgccgagcgcacggctata aacactcctattcaggggacagccgctgatattatcaagctcgccatg ataaaaattcaccggatttttaaagaaaaaggctttgggacaaggatg cttcttcaggtgcatgacgagcttattttgaagcgccaaaagagatt gaagaaatccagccaattgtccgacaaatcatggaaggagtggttgaa ttgaaggttcctctaaaagtaaacctggcaatagggaaaaattgggca gaggcaaaggcataa.
```

The nucleotide of SEQ ID NO:3 encodes the *T. indicus* DNA polymerase I Large fragment of SEQ ID NO:1 as follows:

```
  1 atgggcctcttaaaggaacttccagctactaaaaccctttcgatgaccagatacgagctg
  1  M  G  L  L  K  E  L  P  A  T  K  T  L  S  M  T  R  Y  E  L 61 gttcttgacccggataaagtaaaagaaattgtagaaaaggccaaggggccgaagtggtg
 21  V  L  D  P  D  K  V  K  E  I  V  E  K  A  K  G  A  E  V  V 121 gctattgaccttgaaagtgatacgaaagaccccatgcgtgggaaaatagtagggtctcg
 41  A  I  D  L  E  S  D  T  K  D  P  M  R  G  K  I  V  G  V  S 181 ctttgttttaacccgcccaaagcctattatttccttttagacatgaaggccttgaggcc
 61  L  C  F  N  P  P  K  A  Y  Y  F  P  F  R  H  E  G  L  E  A 241 caaaagcagcttccctgggaggcctttactcatctggccagcctcattgaagacccctca
 81  Q  K  Q  L  P  W  E  A  F  T  H  L  A  S  L  I  E  D  P  S 301 gttaaaaagataggccacaatatcaagtatgacttgattattcttgctcgctacggcgta
101  V  K  K  I  G  H  N  I  K  Y  D  L  I  I  L  A  R  Y  G  V 361 actttaaagggccttgaaggggataccatgctggcttcgtatctccttgatccaacacgt
121  T  L  K  G  L  E  G  D  T  M  L  A  S  Y  L  L  D  P  T  R 421 cgtacccacggccttgatgagctggccgaagaggtcctggggcataccatgattttttac
141  R  T  H  G  L  D  E  L  A  E  E  V  L  G  H  T  M  I  F  Y
```

```
481 aaggaagtgactaaagaactggccaaaggagagctttgccagggtcccctcttgaaaag
161  K  E  V  T  K  E  L  A  K  G  E  S  F  A  R  V  P  L  E  K 541 gcaaagtttacgcctgtgaagacgcccacgttacctatctgctttatcaatatttctgg
181  A  K  V  Y  A  C  E  D  A  H  V  T  Y  L  L  Y  Q  Y  F  W 601 cccaaactcaaagaggaaagcctctggaaggtctttacggaaattgatcgacctttaata
201  P  K  L  E  E  S  L  W  K  V  F  T  E  I  D  R  P  L  I 661 gaagttttggcccacatggaaatggtaggtattaagattgacaccgcctatcttagagga
221  E  V  L  A  H  M  E  M  V  G  I  K  I  D  T  A  Y  L  R  G 721 ctttcgcgagaaatggctgaaaagttaaaggagcttgaagaaaaaatttacaccctggct
241  L  S  R  E  M  A  E  K  L  K  E  L  E  E  K  I  Y  T  L  A 781 ggtgaaaaatttaatatcaattccagcaaacaactgggccagattttatttgaaaagcta
261  G  E  K  F  N  I  N  S  S  K  Q  L  G  Q  I  L  F  E  K  L 841 aaactccctacggttaaaaagaccccaaaaaaaacggcctattcaacggataacgaagta
281  K  L  P  T  V  K  K  T  P  K  K  T  A  Y  S  T  D  N  E  V 901 ttagaggaactttctgcggtccacgaacttccgcgtctgatacttgagtatagaactctg
301  L  E  E  L  S  A  V  H  E  L  P  R  L  I  L  E  Y  R  T  L 961 gctaaactcaaatctacttatgttgatgccctcccgaagatggttaatcctgaaactggt
321  A  K  L  K  S  T  Y  V  D  A  L  P  K  M  V  N  P  E  T  G 1021 cgtcttcatacttcctttaaccagacggttacggccactggaagactttcaagcagtgac
341  R  L  H  T  S  F  N  Q  T  V  T  A  T  G  R  L  S  S  S  D 1081 cctaatcttcaaaatattcctgtgcgtggtgaagagggggcttaagattcgccaggccttt
361  P  N  L  Q  N  I  P  V  R  G  E  E  G  L  K  I  R  Q  A  F 1141 gtgccggaggagattttttgctgccgattacactcagatcgatctgcgagttttagcccat
381  V  P  E  E  I  F  A  A  D  Y  T  Q  I  D  L  R  V  L  A  H 1201 tactcgggagatgaaaccttgattaaggccttctggcaggggaagacattcaccggcgc
401  Y  S  G  D  E  T  L  I  K  A  F  W  Q  G  E  D  I  H  R  R 1261 acggctgcagaaatttttggtatcccgccagaagaagtaactcctgagatgcggcgtatg
421  T  A  A  E  I  F  G  I  P  P  E  E  V  T  P  E  M  R  R  M 1321 gccaagactataaactttggcattgtttacggcatgagtccttacggtctggcaaagaa
441  A  K  T  I  N  F  G  I  V  Y  G  M  S  P  Y  G  L  A  K  E 1381 ctcaaaattggccgccgtgaggccaaggcctttattgagcgctattttgaacgctaccca
461  L  K  I  G  R  R  E  A  K  A  F  I  E  R  Y  F  E  R  Y  P 1441 ggtgtgaaacgctatatggaacaaatcgtggctgaagcccgagaaaagggctacgtggag
481  G  V  K  R  Y  M  E  Q  I  V  A  E  A  R  E  K  G  Y  V  E 1501 acccttttcggacgcaaaaggcctcttcctgacatcaatagccctaatcgtacggcgcgc
501  T  L  F  G  R  K  R  P  L  P  D  I  N  S  P  N  R  T  A  R 1561 gagtttgccgagcgcacggctataaacactcctattcaggggacagccgctgatattatc
521  E  F  A  E  R  T  A  I  N  T  P  I  Q  G  T  A  A  D  I  I 1621 aagctcgccatgataaaaattcaccggattttttaaagaaaaaggctttgggacaaggatg
541  K  L  A  M  I  K  I  H  R  I  F  K  E  K  G  F  G  T  R  M 1681 cttcttcaggtgcatgacgagcttatttttgaagcgccaaaagagattgaagaaatccag
561  L  L  Q  V  H  D  E  L  I  F  E  A  P  K  E  I  E  E  I  Q 1741 ccaattgtccgacaaatcatggaaggagtggttgaattgaaggttcctctaaaagtaaac
581  P  I  V  R  Q  I  M  E  G  V  V  E  L  K  V  P  L  K  V  N 1801 ctggcaatagggaaaaattgggcagaggcaaaggcatga (SEQ ID NO: 3)
601  L  A  I  G  K  N  W  A  E  A  K  A  *.  (SEQ ID NO: 1)
```

Alternatively, the nucleic acid has the sequence shown below (5'-3'):

(SEQ ID NO: 33)
atgggcctcttaaaggaacttccagctactaaaaaccctttcgtatgac cagtacgagctggttcttgaccccggataaagtaaaagaaattgtagaa aaggccaaaggggccgaagtggtggctattgacctttgaaagtgatacg aaagaccccatgcgtgggaaaatagtaggggtctcgctttgttttaac ccgcccaaagcctattatttccctttttagacatgaaggccttgaggcc caaaagcagcttccctgggaggcctttactcatctggccagcctcatt gaagacccctcagttaaaaagataggccacaatatcaagtatgacttg

```
attattcttgctcgctacggcgtaactttaaagggccttgaaggggat
accatgctggcttcgtatctccttgatccaacacgtcgtacccacggc
cttgatgagctggccgaagaggtcctggggcataccatgttttttaca
aggaagtgactaaagaactggccaaggagagagctttgccagggtcc
ctcttgaaaaggcaaaagtttacgcctgtgaagacgcccacgttacct
atctgctttatcaatatttctggcccaaactcaaagaggaaagcctct
ggaaggtctttacggaaattgatcgaccttaatagaagttttggccc
acatggaaatggtaggtattaagattgacaccgcctatcttagaggac
tttcgcgagaaatggctgaaaagttaaaggagcttgaagaaaaattt
acaccctggctggtgaaaaatttaatatcaattccagcaaacaactgg
gccagattttatttgaaaagctaaaactccctacggttaaaaagaccc
caaaaaaaacggcctattcaacggataacgaagtattagaggaacttt
ctgcggtccacgaacttccgcgtctgatacttgagtatagaactctgg
ctaaactcaaatctacttatgttgatgccctcccgaagatggttaatc
ctgaaactggtcgtcttcatacttcctttaaccagacggttacggcca
ctggaagactttcaagcagtgaccctaatcttcaaaatattcctgtgc
gtggtgaagagggcttaagattcgccaggcctttgtgccggaggaga
```

```
tttttgctgccgattacactcagatcgatctgcgagttttagcccatt
actcgggagatgaaaccttgattaaggccttctggcaggggaagaca
ttcaccggcgcacggctgcagaaattttggtatcccgccagaagaag
taactcctgagatgcggcgtatgccaagactataaactttggcattg
tttacggcatgagtccttacggtctggcgaaagaactcaaaattggcc
gccgtgaggccaaggccttttattgagcgctattttgaacgctacccag
gtgtgaaacgctatatggaacaaatcgtggctgaagcccgagaaaagg
gctacgtggagaccctttcggacgcaaaaggcctcttcctgacatca
atagccctaatcgtacggcgcgcgagtttgccgagcgcacggctataa
acactcctattcagggacagccgctgatattatcaagctcgccatga
taaaaattcaccggatttttaaagaaaaaggctttgggacaaggatgc
ttcttcaggtgcacgacgaacttcttttgaagtgcctgaaaaagaga
ttgaagaaatccagccaattgtccgacaaatcatggaaggagtggttg
aattgaaggttcctctaaaagtaaacctggcaatagggaaaaattggg
cagaggcaaaggcataa.
```

The nucleotide of SEQ ID NO:33 encodes the *T. indicus* polymerase I Large fragment of SEQ ID NO:32 as follows:

```
  1 atgggcctcttaaaggaacttccagctactaaaacccttcgtatgaccagtacgagctg
  1  M  G  L  L  K  E  L  P  A  T  K  T  L  S  Y  D  Q  Y  E  L 61 gttcttgacccggataaagtaaaagaaattgtagaaaaggccaaaggggccgaagtggtg
 21  V  L  D  P  D  K  V  K  E  I  V  E  K  A  K  G  A  E  V  V 121 gctattgaccttgaaagtgatacgaaagaccccatgcgtgggaaaatagtagggtctcg
 41  A  I  D  L  E  S  D  T  K  D  P  M  R  G  K  I  V  G  V  S 181 ctttgttttaacccgcccaaagcctattatttccctttagacatgaaggccttgaggcc
 61  L  C  F  N  P  P  K  A  Y  Y  F  P  P  R  H  E  G  L  E  A 241 caaaagcagcttccctgggaggcctttactcatctggccagcctcattgaagacccctca
 81  Q  K  Q  L  P  W  E  A  F  T  H  L  A  S  L  I  E  D  P  S 301 gttaaaaagataggccacaatatcaagtatgacttgattattcttgctcgctacggcgta
101  V  K  K  I  G  H  N  I  K  Y  D  L  I  I  L  A  R  Y  G  V 361 actttaaagggccttgaaggggataccatgctggcttcgtatctccttgatccaacacgt
121  T  L  K  G  L  E  G  D  T  M  L  A  S  Y  L  L  D  P  T  R 421 cgtacccacggccttgatgagctggccgaagaggtcctggggcataccatgatttttta
141  R  T  H  G  L  D  E  L  A  E  E  V  L  G  H  T  M  I  F  Y 481 aaggaagtgactaaagaactggccaaggagagagctttgccagggtccctcttgaaaag
161  K  E  V  T  K  E  L  A  K  G  E  S  F  A  R  V  P  L  E  K 541 gcaaaagtttacgcctgtgaagacgcccacgttacctatctgctttatcaatatttctgg
181  A  K  V  Y  A  C  E  D  A  H  V  T  Y  L  L  Y  Q  Y  F  W 601 cccaaactcaaagaggaaagcctctggaaggtctttacggaaattgatcgacctttaata
201  P  K  L  K  E  E  S  L  W  K  V  F  T  E  I  D  R  P  L  I 661 gaagttttggcccacatggaaatggtaggtattaagattgacaccgcctatcttagagga
221  E  V  L  A  H  M  E  M  V  G  I  K  I  D  T  A  Y  L  R  G 721 ctttcgcgagaaatggctgaaaagttaaaggagcttgaagaaaaatttacaccctggct
241  L  S  R  E  M  A  E  K  L  K  E  L  E  E  K  I  Y  T  L  A 781 ggtgaaaaatttaatatcaattccagcaaacaactgggccagattttatttgaaaagcta
261  G  E  K  F  N  I  S  S  K  Q  L  G  Q  I  L  F  E  K  L 841 aaactccctacggttaaaaagaccccaaaaaaaacggcctattcaacggataacgaagta
281  K  L  P  T  V  K  K  T  P  K  K  T  A  Y  S  T  D  N  E  V
```

-continued

```
 901 ttagaggaactttctgcggtccacgaacttccgcgtctgatacttgagtatagaactctg
 301  L  E  E  L  S  A  V  H  E  L  P  R  L  I  L  E  Y  R  T  L 961 gctaaactcaaatctacttatgttgatgccctcccgaagatggttaatcctgaaactggt
 321  A  K  L  K  S  T  Y  V  D  A  L  P  K  M  V  N  P  E  T  G 1021 cgtcttcatacttcctttaaccagacggttacggccactggaagactttcaagcagtgac
 341  R  L  H  T  S  F  N  Q  T  V  T  A  T  G  R  L  S  S  S  D 1081 cctaatcttcaaaatattcctgtgcgtggtgaagaggggcttaagattcgccaggccttt
 361  P  N  L  Q  N  I  P  V  R  G  E  E  G  L  K  I  R  Q  A  F 1141 gtgccggaggagattttgtgccgattacactcagatcgatctgcgagttttagcccat
 381  V  P  E  E  I  F  A  A  D  Y  T  Q  I  D  L  R  V  L  A  H 1201 tactcgggagatgaaaccttgattaaggccttctggcaggggaagacattcaccggcgc
 401  Y  S  G  D  E  T  L  I  K  A  F  W  Q  G  E  D  I  H  R  R 1261 acggctgcagaattttggtatcccgccagaagaagtaactcctgagatgcggcgtatg
 421  T  A  A  E  I  F  G  I  P  P  E  E  V  T  P  E  M  R  R  M 1321 gccaagactataaactttggcattgtttacggcatgagtccttacggtctggcgaaagaa
 441  A  K  T  I  N  F  G  I  V  Y  G  M  S  P  Y  G  L  A  K  E 1381 ctcaaaattggccgccgtgaggccaaggcctttattgagcgctattttgaacgctaccca
 461  L  K  I  G  R  R  E  A  K  A  F  I  E  R  Y  F  E  R  Y  P 1441 ggtgtgaaacgctatatggaacaaatcgtggctgaagcccgagaaaagggctacgtggag
 481  G  V  K  R  Y  M  E  Q  I  V  A  E  A  R  E  K  G  Y  V  E 1501 accctttcggacgcaaaaggcctcttcctgacatcaatagccctaatcgtacggcgcgc
 501  T  L  F  G  R  K  R  P  L  P  D  I  N  S  P  N  R  T  A  R 1561 gagtttgccgagcgcacggctataaacactcctattcaggggacagccgctgatattatc
 521  E  F  A  E  R  T  A  I  N  T  P  I  Q  G  T  A  A  D  I  I 1621 aagctcgccatgataaaaattcaccggattttaaagaaaaaggctttgggacaaggatg
 541  K  L  A  M  I  K  I  H  R  I  F  K  E  K  G  F  G  T  R  M 1681 cttcttcaggtgcacgacgaacttctttttgaagtgcctgaaaaagagattgaagaaatc
 561  L  L  Q  V  H  D  E  L  L  F  E  V  P  E  K  E  I  E  E  I 1741 cagccaattgtccgacaaatcatggaaggagtggttgaattgaaggttcctctaaaagta
 581  Q  P  I  V  R  Q  I  M  E  G  V  V  E  L  K  V  P  L  K  V 1801 aacctggcaataggggaaaaattgggcagaggcaaaggcataa (SEQ ID NO: 33)
 601  N  L  A  I  G  K  N  W  A  E  A  K  A  *. (SEQ ID NO: 32)
```

The invention further provides an isolated nucleic acid encoding the polypeptide with identity to the *T. indicus* full length DNA polymerase I. The nucleic acid may, for example, have a sequence as shown below (5'-3'):

(SEQ ID NO: 4)
atggcgcagaaaagcttgtttcctaaaaaaattaccatttaaagatgat aaagacccatcttcgttattgacgggagttcttttgtttaccgggct tactatgccataagagggcatctatcaaaccgcaaagggctcccaacc aaggcggtctttgggtttacccagatgcttttaaagcttttgcgtgag atgaaccctgagtatgtggtggtgtgctttgacgccaaagggcctact tttcgccacgagatgtacaaagaatacaaagccaaccgccccccatg ccagatgatctttccgtccagattccctatatcaaagaggtaaccagg gcctttggagtccctattcttgaaatagaaggctttgaagctgacgat ctcatcgccgctattgccactcgtatggaaagaccaattgtcatcgtt ggtgagataaagatttgttcccccttatttcagagaaagttgtcatg tgggaccccatgaaagacgaactgattgacgaaagctggataaagaaa cgttttggcattgaacctaaaaagctccttgatgtaagggcccttgcc ggcgatagcattgataacgtgccaggggttccgggtattggtgaaaaa acggccctaaggctcataaaagaatacggttcccttgaagaagtcctt aaccatgccgaagaaataaaacaaaagcgcttgcgtgaaaacctcatc aaacacgccggagacgcccttatttccaaaaaactggttgagcttgag gccaaagccccaatcccccttgagcctgattttaccgcaaacggcca ttaaatgccctaaaactaagggaactcttccttgagcttgaatttaaa aagctcttaaaggaacttccagctactaaaaccctttcgatgaccaga tacgagctggttcttgacccggataaagtaaaagaaattgtagaaaag gccaaaggggccgaagtggtggctattgaccttgaaagtgatacgaaa gaccccatgcgtgggaaaatagtaggggtctcgctttgttttaacccg cccaaagcctattatttccttttagacatgaaggccttgaggcccaa aagcagcttccctgggaggcctttactcatctggccagcctcattgaa gaccctcagttaaaaagataggccacaatatcaagtatgacttgatt attcttgctcgctacggcgtaacttttaaagggccttgaaggggatacc

```
atgctggcttcgtatctccttgatccaacacgtcgtacccacggcctt
gatgagctggccgaagaggtcctggggcataccatgattttttacaag
gaagtgactaaagaactggccaaaggagagagctttgccagggtccct
cttgaaaaggcaaaagtttacgcctgtgaagacgcccacgttacctat
ctgctttatcaatatttctggcccaaactcaaagaggaaagcctctgg
aaggtctttacggaaattgatcgacctttaatagaagttttggcccac
atggaaatggtaggtattaagattgacaccgcctatcttagaggactt
tcgcgagaaatggctgaaaagttaaaggagcttgaagaaaaaatttac
accctggctggtgaaaaatttaatatcaattccagcaaacaactgggc
cagattttatttgaaaagctaaaactccctacggttaaaaagacccca
aaaaaaacggcctattcaacggataacgaagtattagaggaactttct
gcggtccacgaacttccgcgtctgatacttgagtatagaactctggct
aaactcaaatctacttatgttgatgccctcccgaagatggttaatcct
gaaactggtcgtcttcatacttcctttaaccagacggttacggccact
ggaagactttcaagcagtgaccctaatcttcaaaatattcctgtgcgt
ggtgaagagggggcttaagattcgccaggcctttgtgccggaggagatt
tttgctgccgattacactcagatcgatctgcgagttttagcccattac
tcgggagatgaaaccttgattaaggccttctggcaggggaagacatt
caccggcgcacggctgcagaaattttttggtatcccgccagaagaagta
actcctgagatgcggcgtatggccaagactataaacttttggcattgtt
tacggcatgagtccttacggtctggcgaaagaactcaaaattggccgc
cgtgaggccaaggcctttattgagcgctattttgaacgctacccaggt
gtgaaacgctatatggaacaaatcgtggctgaagcccgagaaagggc
tacgtggagaccattttcggacgcaaaaggcctcttcctgacatcaat
agccctaatcgtacggcgcgcgagtttgccgagcgcacggctataaac
actcctattcaggggacaccgctgatattatcaagctcgccatgata
aaaattcaccggatttttaaagaaaaaggctttgggacaaggatgctt
cttcaggtgcatgacgagatatttttgaagcgcctgaaaaagagattg
aagaaatccagccaattgtccgacaaatcatggaaggagtggttgaat
tgaaggttcctctaaaagtaaacctggcaatagggaaaaattgggcag
aggcaaaggcataa.
```

The nucleotide of SEQ ID NO:4 encodes the *T. indicus* full length DNA polymerase I of SEQ ID NO:2 as follows:

```
  1 atggctcaaaaaagtttgtttcctaaaaaattaccatttaaagatgataaagacccatc
  1  M  A  Q  K  S  L  F  P  K  K  L  P  F  K  D  D  K  D  P  I 61 ttcgttattgacgggagttcttttgtttaccgggcttactatgccataagagggcatcta
 21  F  V  I  D  G  S  S  F  V  Y  R  A  Y  Y  A  I  R  G  H  L 121 tcaaaccgcaaaggctcccaaccaaggcggtctttgggtttacccagatgcttttaaag
 41  S  N  R  K  G  L  P  T  K  A  V  F  G  F  T  Q  M  L  L  K 181 cttttgcgtgagatgaaccctgagtatgtggtggtgtgctttgacgccaaagggcctact
 61  L  L  R  E  M  N  P  E  Y  V  V  V  C  F  D  A  K  G  P  T 241 tttcgccacgagatgtacaaagaatacaaagccaaccgcccccccatgccagatgatctt
 81  F  R  H  E  M  Y  K  E  Y  K  A  N  R  P  P  M  P  D  D  L 301 tccgtccagattccctatatcaaagaggtaaccagggcctttggagtccctattcttgaa
101  S  V  Q  I  P  Y  I  K  E  V  T  R  A  F  G  V  P  I  L  E 361 atagaaggctttgaagctgacgatctcatcgccgctattgccactcgtatggaaagacca
121  I  E  G  F  E  A  D  D  L  I  A  A  I  A  T  R  M  E  R  P 421 attgtcatcgttggtggagataaagatttgttccccttatttcagagaaagttgtcatg
141  I  V  I  V  G  G  D  K  D  L  F  P  L  I  S  E  K  V  V  M 481 tgggacccatgaaagacgaactgattgacgaaagctggataaagaaacgttttggcatt
161  W  D  P  M  K  D  E  L  I  D  E  S  W  I  K  K  R  F  G  I 541 gaacctaaaaagctccttgatgtaagggcccttgccggcgatagcattgataacgtgcca
181  E  P  K  K  L  L  D  V  R  A  L  A  G  D  S  I  D  N  V  P 601 ggggttccgggtattggtgaaaaaacggccctaaggctcataaaagaatacggttccctt
201  G  V  P  G  I  G  E  K  T  A  L  R  L  I  K  E  Y  G  S  L 661 gaagaagtccttaaccatgccgaagaaataaaacaaaagcgcttgcgtgaaaacctcatc
221  E  E  V  L  N  H  A  E  E  I  K  Q  K  R  L  R  E  N  L  I 721 aaacacgccggagacgcccttatttccaaaaaactggttgagcttgaggccaaagcccca
241  K  H  A  G  D  A  L  I  S  K  K  L  V  E  L  E  A  K  A  P 781 atccccccttgagcctgattttaccgcaaacggccattaaatgccctaaaactaagggaa
261  I  P  L  E  P  D  F  Y  R  K  R  P  L  N  A  L  K  L  R  E 841 ctcttccttgagcttgaatttaaaaagctcttaaaggaacttccagctactaaaaccctt
281  L  F  L  E  L  E  F  K  K  L  L  K  E  L  P  A  T  K  T  L
```

-continued

```
 901 tcgatgaccagatacgagctggttcttgacccggataaagtaaaagaaattgtagaaaag
 301  S  M  T  R  Y  E  L  V  L  D  P  D  K  V  K  E  I  V  E  K 961 gccaaggggccgaagtggtggctattgaccttgaaagtgatacgaaagaccccatgcgt
 321  A  K  G  A  E  V  V  A  I  D  L  E  S  D  T  K  D  P  M  R 1021 gggaaaatagtaggggtctcgctttgttttaacccgcccaaagcctattatttccctttt
 341  G  K  I  V  G  V  S  L  C  F  N  P  P  K  A  Y  Y  F  P  F 1081 agacatgaaggccttgaggcccaaaagcagcttccctgggaggcctttactcatctggcc
 361  R  H  E  G  L  E  A  Q  K  Q  L  P  W  E  A  F  T  H  L  A 1141 agcctcattgaagacccctcagttaaaaagataggccacaatatcaagtatgacttgatt
 381  S  L  I  E  D  P  S  V  K  K  I  G  H  N  I  K  Y  D  L  I 1201 attcttgctcgctacggcgtaactttaaaggggcttgaaggggataccatgctggcttcg
 401  I  L  A  R  Y  G  V  T  L  K  G  L  E  G  D  T  M  L  A  S 1261 tatctccttgatccaacacgtcgtacccacggccttgatgagctggccgaagaggtcctg
 421  Y  L  L  D  P  T  R  R  T  H  G  L  D  E  L  A  E  E  V  L 1321 gggcataccatgatttttacaaggaagtgactaaagaactggccaaaggagagagcttt
 441  G  H  T  M  I  F  Y  K  E  V  I  K  E  L  A  K  G  E  S  F 1381 gccagggtccctcttgaaaaggcaaaagtttacgcctgtgaagacgcccacgttacctat
 461  A  R  V  P  L  E  K  A  K  V  Y  A  C  E  D  A  H  V  T  Y 1441 ctgctttatcaatatttctggcccaaactcaaagaggaaagcctctggaaggtctttacg
 481  L  L  Y  Q  Y  F  W  P  K  L  K  E  E  S  L  W  K  V  F  T 1501 gaaattgatcgacctttaatagaagttttggcccacatggaaatggtaggtattaagatt
 501  E  I  D  R  P  L  I  E  V  L  A  H  M  E  M  V  G  I  K  I 1561 gacaccgcctatcttagaggactttcgcgagaaatggctgaaaagttaaaggagcttgaa
 521  D  T  A  Y  L  R  G  L  S  R  E  M  A  E  K  L  K  E  L  E 1621 gaaaaaatttacaccctggctggtgaaaaatttaatatcaattccagcaaacaactgggc
 541  E  K  I  Y  T  L  A  G  E  K  F  N  I  N  S  S  K  Q  L  G 1681 cagattttatttgaaaagctaaaactccctacggttaaaaagaccccaaaaaaaacggcc
 561  Q  I  L  F  E  K  L  K  L  P  T  V  K  K  T  P  K  K  T  A 1741 tattcaacggataacgaagtattagaggaactttctgcggtccacgaacttccgcgtctg
 581  Y  S  T  D  N  E  V  L  E  E  L  S  A  V  H  E  L  P  R  L 1801 atacttgagtatagaactctggctaaactcaaatctacttatgttgatgccctcccgaag
 601  I  L  E  Y  R  T  L  A  K  L  K  S  T  Y  V  D  A  L  P  K 1861 atggttaatcctgaaactggtcgtcttcatacttcctttaaccagacggttacggccact
 621  M  V  N  P  E  T  G  R  L  H  T  S  F  N  Q  T  V  T  A  T 1921 ggaagactttcaagcagtgaccctaatcttcaaaatattcctgtgcgtggtgaagagggg
 641  G  R  L  S  S  S  D  P  N  L  Q  N  I  P  V  R  G  E  E  G 1981 cttaagattcgccaggcctttgtgccggaggagattttgctgccgattacactcagatc
 661  L  K  I  R  Q  A  F  V  P  E  E  I  F  A  A  D  Y  T  Q  I 2041 gatctgcgagttttagcccattactcgggagatgaaaccttgattaaggccttctggcag
 681  D  L  R  V  L  A  H  Y  S  G  D  E  T  L  I  K  A  F  W  Q 2101 ggggaagacattcaccggcgcacggctgcagaaattttggtatcccgccagaagaagta
 701  G  E  D  I  H  R  R  T  A  A  E  I  F  G  I  P  P  E  E  V 2161 actcctgagatgcggcgtatggccaagactataaactttggcattgtttacggcatgagt
 721  T  P  E  M  R  R  M  A  K  T  I  N  F  G  I  V  Y  G  M  S 2221 ccttacggtctggcgaaagaactcaaaattggccgccgtgaggccaaggcctttattgag
 741  P  Y  G  L  A  K  E  L  K  I  G  R  R  E  A  K  A  F  I  E 2281 cgctattttgaacgctaccaggtgtgaaacgctatatggaacaaatcgtggctgaagcc
 761  R  Y  F  E  R  Y  P  G  V  K  R  Y  M  E  Q  I  V  A  E  A 2341 cgagaaaagggctacgtggagaccctttcggacgcaaaaggcctcttcctgacatcaat
 781  R  E  K  G  Y  V  E  T  L  F  G  R  K  R  P  L  P  D  I  N 2401 agccctaatcgtacggcgcgcgagtttgccgagcgcacggctataaacactcctattcag
 801  S  P  N  R  T  A  R  E  F  A  E  R  T  A  I  N  T  P  I  Q 2461 gggacagccgctgatattatcaagctcgccatgataaaaattcaccggatttttaaagaa
 821  G  T  A  A  D  I  I  K  L  A  M  I  K  I  H  R  I  F  K  E
```

```
2521 aaaggctttgggacaaggatgcttcttcaggtgcatgacgagcttattttttgaagcgcct
 841  K  G  F  G  T  R  M  L  L  Q  V  H  D  E  L  I  F  E  A  P 2581 gaaaaagagattgaagaaatccagccaattgtccgacaaatcatggaaggagtggttgaa
 861  E  K  E  I  E  E  I  Q  P  I  V  R  Q  I  M  E  G  V  V  E 2641 ttgaaggttcctctaaaagtaaacctggcaatagggaaaaattgggcagaggcaaaggca
 881  L  K  V  P  L  K  V  N  L  A  I  G  K  N  W  A  E  A  K  A 2701 taa (SEQ ID NO: 4)
 901  *. (SEQ ID NO: 2)
```

Alternatively, the nucleic acid has the sequence shown below (5'-3'):

(SEQ ID NO: 35)
atggcgcagaaaagcttgtttcctaaaaaattaccatttaaagatgat
aaagaccccatcttcgttattgacgggagttcttttgtttaccgggct
tactatgccataagagggcatctatcaaaccgcaaagggctcccaacc
aaggcggtcttttgggtttacccagatgcttttaaagcttttgcgtgag
atgaaccctgagtatgtggtggtgtgcttttgacgccaaagggcctact
tttcgccacgagatgtacaaagaatacaaagccaaccgcccccccatg
ccagatgatcttccgtccagattccctatatcaaagaggtaaccagg
gcctttggagtccctattcttgaaatagaaggctttgaagctgacgat
ctcatcgccgctattgccactcgtatggaaagaccaattgtcatcgtt
ggtggagataaagatttgttcccccttatttcagagaaagttgtcatg
tgggaccccatgaaagacgaactgattgacgaaagctggataaagaaa
cgttttggcattgaacctaaaaagctccttgatgtaagggcccttgcc
ggcgatagcattgataacgtgccaggggttccgggtattggtgaaaaa
acggccctaaggctcataaaagaatacggttcccttgaagaagtcctt
aaccatgccgaagaaataaaacaaaagcgcttgcgtgaaaacctcatc
aaacacgccggagacgcccttatttccaaaaaactggttgagcttgag
gccaaagcccaatccccttgagcctgatttttaccgcaaacggcca
ttaaatgccctaaaactaagggaactcttccttgagcttgaatttaaa
aagctcttaaaggaacttccagctactaaaacccttttcgtatgaccag
tacgagctggttcttgaccggataaagtaaaagaaattgtagaaaag
gccaaaggggccgaagtggtggctattgaccttgaaagtgatacgaaa
gaccccatgcgtgggaaaatagtagggtctcgctttgttttaaaccg
cccaaagcctattatttccttttagacatgaaggccttgaggcccaa
aagcagatccctgggaggcctttactcatctggccagcctcattgaag
accccctcagttaaaaagataggccacaatatcaagtatgacttgatta
ttcttgctcgctacggcgtaactttaaagggccttgaaggggatacca
tgctggatcgtataccttgatccaacacgtcgtacccacggccttgat
gagctggccgaagaggtcctggggcataccatgatttttttacaaggaa
gtgactaaagaactggccaaaggagagagctttgccagggtccctctt
gaaaaggcaaaagtttacgcctgtgaagacgcccacgttacctatctg
ctttatcaatatttctggcccaaactcaaagaggaaagcctctggaag
gtctttacggaaattgatcgacctttaatagaagttttggcccacatg
gaaatggtaggtattaagattgacaccgcctatcttagaggactttcg
cgagaaatggctgaaaagttaaaggagcttgaagaaaaatttacacc
ctggctggtgaaaatttaatatcaattccagcaaacaactgggccag
attttatttgaaaagctaaaactccctacggttaaaaagaccccaaaa
aaaacggcctattcaacggataacgaagtattagaggaactttctgcg
gtccacgaacttccgcgtctgatacttgagtatagaactctggctaaa
ctcaaatctacttatgttgatgccctcccgaagatggttaatcctgaa
actggtcgtcttcatacttcctttaaccagacggttacggccactgga
agactttcaagcagtgaccctaatcttcaaaatattcctgtgcgtggt
gaagaggggataagattcgccaggcctttgtgccggaggagattttgc
tgccgattacactcagatcgatctgcgagttttagcccattactcggg
agatgaaaccttgattaaggccttctggcaggggggaagacattcaccg
gcgcacggctgcagaaatttttggtatcccgccagaagaagtaactcc
tgagatgcggcgtatggccaagactataaactttggcattgtttacgg
catgagtccttacggtctggcgaaagaactcaaaattggccgccgtga
ggccaaggcctttattgagcgctattttgaacgctacccaggtgtgaa
acgctatatggaacaaatcgtggctgaagcccgagaaaagggctacgt
ggagacccttttcggacgcaaaaggcctcttcctgacatcaatagccc
taatcgtacggcgcgcgagtttgccgagcgcacggctataaacactcc
tattcagggggacagccgctgatattatcaagctcgccatgataaaaat
tcaccggattttttaaagaaaaaggctttgggacaaggatgcttcttca
ggtgcacgacgaacttctttttgaagtgcctgaaaaagagattgaaga
aatccagccaattgtccgacaaatcatggaaggagtggttgaattgaa
ggttcctctaaaagtaaacctggcaatagggaaaaattgggcagaggc
aaaggcataa.

The nucleotide of SEQ ID NO:35 encodes the *T. indicus* full length DNA polymerase I of SEQ ID NO:34 as follows:

```
1 atggcgcagaaaagcttgtttcctaaaaaattaccatttaaagatgataaagaccccatc
1  M  A  Q  K  S  L  F  P  K  K  L  P  F  K  D  D  K  D  P  I
```

-continued

```
 61 ttcgttattgacgggagttcttttgtttaccgggcttactatgccataagagggcatcta
 21  F  V  I  D  G  S  S  F  V  Y  R  A  Y  Y  A  I  R  G  H  L 121 tcaaaccgcaaagggctcccaaccaaggcggtctttgggtttacccagatgcttttaaag
 41  S  N  R  K  G  L  P  T  K  A  V  F  G  F  T  Q  M  L  L  K 181 cttttgcgtgagatgaaccctgagtatgtggtggtgtgctttgacgccaaagggcctact
 61  L  L  R  E  M  N  P  E  Y  V  V  V  C  F  D  A  K  G  P  T 241 tttcgccacgagatgtacaaagaatacaaagccaaccgcccccccatgccagatgatctt
 81  F  R  H  E  M  Y  K  E  Y  K  A  N  R  P  P  M  P  D  D  L 301 tccgtccagattccctatatcaagaggtaaccagggcctttggagtccctattcttgaa
101  S  V  Q  I  P  Y  I  K  E  V  T  R  A  F  G  V  P  I  L  E 361 atagaaggctttgaagctgacgatctcatcgccgctattgccactcgtatggaaagacca
121  I  E  G  F  E  A  D  D  L  I  A  A  I  A  T  R  M  E  R  P 421 attgtcatcgttggtggagataaagatttgttccccctttatttcagagaaagttgtcatg
141  I  V  I  V  G  G  D  K  D  L  F  P  L  I  S  E  K  V  V  M 481 tgggaccccatgaaagacgaactgattgacgaaagctggataaagaaacgttttggcatt
161  W  D  P  M  K  D  E  L  I  D  E  S  W  I  K  K  R  F  G  I 541 gaacctaaaaagctccttgatgtaagggcccttgccggcgatagcattgataacgtgcca
181  E  P  K  K  L  L  D  V  R  A  L  A  G  D  S  I  D  N  V  P 601 ggggttccggggtattggtgaaaaaacggccctaaggctcataaaagaatacggttccctt
201  G  V  P  G  I  G  E  K  T  A  L  R  L  I  K  E  Y  G  S  L 661 gaagaagtccttaaccatgccgaagaaataaaaacaaaagcgcttgcgtgaaaacctcatc
221  E  E  V  L  N  H  A  E  E  I  K  Q  K  R  L  R  E  N  L  I 721 aaacacgccggagacgcccttatttccaaaaaactggttgagcttgaggccaaagcccca
241  K  H  A  G  D  A  L  I  S  K  K  L  V  E  L  E  A  K  A  P 781 atccccctttgagcctgattttttaccgcaaacggccattaaatgccctaaaactaagggaa
261  I  P  L  E  P  D  F  Y  R  K  R  P  L  N  A  L  K  L  R  E 841 ctcttccttgagcttgaatttaaaaagctcttaaaggaacttccagctactaaaacccttt
281  L  F  L  E  L  F  K  K  L  L  K  E  L  P  A  T  K  T  L 901 tcgtatgaccagtacgagctggttcttgacccggataaagtaaaagaaattgtagaaaag
301  S  Y  D  Q  Y  E  L  V  L  D  P  D  K  V  K  E  I  V  E  K 961 gccaaggggccgaagtggtggctattgaccttgaaagtgatacgaaagaccccatgcgt
321  A  K  G  A  E  V  V  A  I  D  L  E  S  D  T  K  D  P  M  R 1021 gggaaaatagtaggggtctcgctttgttttaacccgcccaaagcctattatttcccttttt
341  G  K  I  V  G  V  S  L  C  F  N  P  P  K  A  Y  Y  F  P  F 1081 agacatgaaggccttgaggccaaaagcagcttccctgggaggcctttactcatctggcc
361  R  H  E  G  L  E  A  Q  K  Q  L  P  W  E  A  F  T  H  L  A 1141 agcctcattgaagacccctcagttaaaaagataggccacaatatcaagtatgacttgatt
381  S  L  I  E  D  P  S  V  K  K  I  G  H  N  I  K  Y  D  L  I 1201 attcttgctcgctacggcgtaactttaaagggccttgaaggggataccatgctggcttcg
401  I  L  A  R  Y  G  V  T  L  K  G  L  E  G  D  T  M  L  A  S 1261 tatctccttgatccaacacgtcgtacccacgccttgatgagctggccgaagaggtcctg
421  Y  L  L  D  P  T  R  R  T  H  G  L  D  E  L  A  E  E  V  L 1321 gggcataccatgattttttacaaggaagtgactaaagaactggccaaaggagagagcttt
441  G  H  T  M  I  F  Y  K  E  V  T  K  E  L  A  K  G  E  S  F 1381 gccagggtcccctcttgaaaaggcaaaagtttacgcctgtgaagacgcccacgttacctat
461  A  R  V  P  L  E  K  A  K  V  Y  A  C  E  D  A  H  V  T  Y 1441 ctgctttatcaatatttctggcccaaactcaaagaggaaagcctctggaaggtctttacg
481  L  L  Y  Q  Y  F  W  P  K  L  K  E  E  S  L  W  K  V  F  T 1501 gaaattgatcgacctttaatagaagttttggcccacatggaaatggtaggtattaagatt
501  E  I  D  R  P  L  I  E  V  L  A  H  M  E  M  V  G  I  K  I 1561 gacaccgcctatcttagaggactttcgcgagaaatggctgaaaagttaaaggagcttgaa
521  D  T  A  Y  L  R  G  L  S  R  E  M  A  E  K  L  K  E  L  E 1621 gaaaaaatttacacccctggctggtgaaaaaatttaatatcaattccagcaaacaactgggc
541  E  K  I  Y  T  L  A  G  E  K  E  N  I  N  S  S  K  Q  L  G
```

-continued

```
1681 cagattttatttgaaaagctaaaactccctacggttaaaaagaccccaaaaaaaacggcc
 561  Q  I  L  F  E  K  L  K  L  P  T  V  K  K  T  P  K  K  T  A 1741 tattcaacggataacgaagtattagaggaactttctgcggtccacgaacttccgcgtctg
 581  Y  S  T  D  N  E  V  L  E  E  L  S  A  V  H  E  L  P  R  L 1801 atacttgagtatagaactctggctaaactcaaatctacttatgttgatgccctcccgaag
 601  I  L  E  Y  R  T  L  A  K  L  K  S  T  Y  V  D  A  L  P  K 1861 atggtaatcctgaaactggtcgtcttcatacttcctttaaccagacggttacggccact
 621  M  V  N  P  E  T  G  R  L  H  T  S  F  N  Q  T  V  T  A  T 1921 ggaagactttcaagcagtgaccctaatcttcaaaatattcctgtgcgtggtgaagagggg
 641  G  R  L  S  S  S  D  P  N  L  Q  N  I  P  V  R  G  E  E  G 1981 cttaagattcgccaggcctttgtgccggaggagattttgctgccgattacactcagatc
 661  L  K  I  R  Q  A  F  V  P  E  E  I  F  A  A  D  Y  T  Q  I 2041 gatctgcgagttttagcccattactcgggagatgaaaccttgattaaggccttctggcag
 681  D  L  R  V  L  A  H  Y  S  G  D  E  T  L  I  K  A  F  W  Q 2101 ggggaagacattcaccggcgcacggctgcagaaattttggtatcccgccagaagaagta
 701  G  E  D  I  H  R  R  T  A  A  E  I  E  G  I  P  P  E  E  V 2161 actcctgagatgcggcgtatggccaagactataaactttggcattgtttacggcatgagt
 721  T  P  E  M  R  R  M  A  K  T  I  N  F  G  I  V  Y  G  M  S 2221 ccttacggtctggcgaaagaactcaaaattggccgccgtgaggccaaggcctttattgag
 741  P  Y  G  L  A  K  E  L  K  I  G  R  R  E  A  K  A  F  I  E 2281 cgctattttgaacgctacccaggtgtgaaacgctatatggaacaaatcgtggctgaagcc
 761  R  Y  F  E  R  Y  P  G  V  K  R  Y  M  E  Q  I  V  A  E  A 2341 cgagaaagggctacgtggagaccctttcggacgcaaaaggcctcttcctgacatcaat
 781  R  E  K  G  Y  V  E  T  L  F  G  R  K  R  P  L  P  D  I  N 2401 agccctaatcgtacggcgcgcgagtttgccgagcgcacggctataaacactcctattcag
 801  S  P  N  R  T  A  R  E  F  A  E  R  T  A  I  N  T  P  I  Q 2461 gggacagccgctgatattatcaagctcgccatgataaaaattcaccggattttaaagaa
 821  G  T  A  A  D  I  I  K  L  A  M  I  K  I  H  R  I  F  K  E 2521 aaaggctttgggacaaggatgcttcttcaggtgcacgacgaacttcttttgaagtgcct
 841  K  G  F  G  T  R  M  L  L  Q  V  H  D  E  L  L  F  E  V  P 2581 gaaaaagagattgaagaaatccagccaattgtccgacaaatcatggaaggagtggttgaa
 861  E  K  E  I  E  E  I  Q  P  I  V  R  Q  I  M  E  G  V  V  E 2641 ttgaaggttcctctaaaagtaaacctggcaatagggaaaaattgggcagaggcaaaggca
 881  L  K  V  P  L  K  V  N  L  A  I  G  K  N  W  A  E  A  K  A 2701 taa (SEQ ID NO: 35)
 901  *.  (SEQ ID NO: 34)
```

Also encompassed by the invention are variants of the nucleic acids, as defined below.

Further provided is a vector comprising the isolated nucleic acid as described herein.

Additionally provided is a host cell transformed with the nucleic acid or the vector of the invention.

A recombinant polypeptide expression from the host cell is also encompassed by the invention.

In another aspect of the invention there is provided a kit comprising the polypeptide as described herein and/or the composition described herein and/or the isolated nucleic acid as described herein and/or the vector as described herein and/or the host cell as described herein, together with packaging materials therefor. The kit may, for example, comprise components including the polypeptide for carrying out a reaction requiring DNA polymerase activity, such as PCR or LAMP.

The invention further provides a method of amplifying a sequence of a target nucleic acid using a thermocycling reaction, for example PCR, comprising the steps of:
(1) contacting the target nucleic acid with the polypeptide having thermostable DNA polymerase activity as described herein; and
(2) incubating the target nucleic acid with the polypeptide under thermocycling reaction conditions which allow amplification of the target nucleic acid.

Another aspect of the invention encompasses a method of amplifying a sequence of a target nucleic acid using an isothermal reaction, for example LAMP, comprising the steps of:
(1) contacting the target nucleic acid with the polypeptide having thermostable DNA polymerase activity as described herein; and
(2) incubating the target nucleic acid with the polypeptide under isothermal reaction conditions which allow amplification of the target nucleic acid.

The present invention also encompasses structural variants of the polypeptides as defined herein. As used herein, a "variant" means a polypeptide in which the amino acid sequence differs from the base sequence from which it is derived in that one or more amino acids within the sequence are substituted for other amino acids. Amino acid substitutions may be regarded as "conservative" where an amino acid is replaced with a different amino acid with broadly similar properties.

Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Non-conservative substitutions are possible provided that these do not interrupt with the function of the DNA binding domain polypeptides.

Broadly speaking, fewer non-conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the thermostable DNA polymerase activity according to the invention. For example, when determining whether a variant of the polypeptide falls within the scope of the invention, the skilled person will determine whether the variant retains enzyme activity (i.e., polymerase activity) at least 60%, preferably at least 70%, more preferably at least 80%, yet more preferably 90%, 95%, 96%, 97%, 98%, 99% or 100% of the non-variant polypeptide. Activity may be measured by, for example, any standard measure such as the number of bases of a template sequence which can be replicated in a given time period.

Suitably, variants may have a sequence which is at least 55% identical, 60% identical, 65% identical, for example at least 70% or 75% identical, such as at least 80%, 85%, 90%, 95%, 96%, 97%, 98% or even 99% identical to the sequence of any of SEQ ID NOs:1, 2, 32 or 34.

For example, the invention encompasses a polypeptide having thermostable DNA polymerase activity and comprising or consisting essentially of an amino acid sequence of SEQ ID NOs: 1, 2, 32 or 34 with up to about one third of the amino acid sequence from the N- or C-terminus having been deleted, or having at least 55% sequence identity to such a sequence. For example, up to about 300 amino acids may be removed from either the N- or C-terminus of SEQ ID NOs:2 or 34; up to about 205 amino acids may be removed from either the N- or C-terminus of SEQ ID NOs:1 or 32.

Using the standard genetic code, further nucleic acids encoding the polypeptides may readily be conceived and manufactured by the skilled person. The nucleic acid may be DNA or RNA, and where it is a DNA molecule, it may for example comprise a cDNA or genomic DNA.

The invention encompasses variant nucleic acids encoding the polypeptides of the invention. The term "variant" in relation to a nucleic acid sequences means any substitution of, variation of, modification of, replacement of, deletion of, or addition of one or more nucleic acid(s) from or to a polynucleotide sequence providing the resultant polypeptide sequence encoded by the polynucleotide exhibits at least the same properties as the polypeptide encoded by the basic sequence. The term therefore includes allelic variants and also includes a polynucleotide which substantially hybridises to the polynucleotide sequence of the present invention. Such hybridisation may occur at or between low and high stringency conditions. In general terms, low stringency conditions can be defined a hybridisation in which the washing step takes place in a 0.330-0.825 M NaCl buffer solution at a temperature of about 40-48° C. below the calculated or actual melting temperature ($T_m$) of the probe sequence (for example, about ambient laboratory temperature to about 55° C.), while high stringency conditions involve a wash in a 0.0165-0.0330 M NaCl buffer solution at a temperature of about 5-10° C. below the calculated or actual $T_m$ of the probe(for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (1989; Molecular Cloning, Cold Spring Harbor Laboratory Press, Cold Spring Harbor).

Typically, variants have 55% or more of the nucleotides in common with the nucleic acid sequence of the present invention, more typically 60%, 65%, 70%, 80%, 85%, or even 90%, 95%, 98% or 99% or greater sequence identity.

Variant nucleic acids of the invention may be codon-optimised for expression in a particular host cell.

DNA polymerases and nucleic acids of the invention may be prepared synthetically using conventional synthesizers. Alternatively, they may be produced using recombinant DNA technology or isolated from natural sources followed by any chemical modification, if required. In these cases, a nucleic acid encoding the chimeric protein is incorporated into a suitable expression vector, which is then used to transform a suitable host cell, such as a prokaryotic cell such as E. coli. The transformed host cells are cultured and the protein isolated therefrom. Vectors, cells and methods of this type form further aspects of the present invention.

Sequence identity between nucleotide and amino acid sequences can be determined by comparing an alignment of the sequences. When an equivalent position in the compared sequences is occupied by the same amino acid or base, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

In addition to the BLASTP program mentioned above, further suitable computer programs for carrying out sequence comparisons are widely available in the commercial and public sector. Examples include the MatGat program (Campanella et al., 2003, BMC Bioinformatics 4: 29), the Gap program (Needleman & Wunsch, 1970, J. Mol. Biol. 48: 443-453) and the FASTA program (Altschul et al., 1990, J. Mol. Biol. 215: 403-410). MatGAT v2.03 is freely available and has also been submitted for public distribution to the Indiana University Biology Archive (IUBIO Archive). Gap and FASTA are available as part of the Accelrys GCG Package Version 11.1 (Accelrys, Cambridge, UK), formerly known as the GCG Wisconsin Package. The FASTA program can alternatively be accessed publically from the European Bioinformatics Institute and the University of Virginia. FASTA may be used to search a sequence database with a given sequence or to compare two given sequences. Typically, default parameters set by the computer programs should be used when comparing sequences. The default parameters may change depending on the type and length of sequences being compared. A sequence comparison using the MatGAT program may use default parameters of Scoring Matrix=Blosum50, First Gap=16, Extending Gap=4 for DNA, and Scoring Matrix=Blosum50, First Gap=12, Extending Gap=2 for protein. A comparison using the FASTA program may use default parameters of Ktup=2, Scoring matrix=Blosum50, gap=−10 and ext=−2.

In one aspect of the invention, sequence identity is determined using the MatGAT program v2.03 using default parameters as noted above.

As used herein, a "DNA polymerase" refers to any enzyme that catalyzes polynucleotide synthesis by addition of nucleotide units to a nucleotide chain using a nucleic acid such as DNA as a template. The term includes any variants and recombinant functional derivatives of naturally occurring nucleic acid polymerases, whether derived by genetic modification or chemical modification or other methods known in the art.

As used herein, "thermostable" DNA polymerase activity means DNA polymerase activity which is relatively stable to heat and which functions at high temperatures, for example 45-100° C., preferably 55-100° C., 65-100° C., 75-100° C., 85-100° C. or 95-100° C., as compared, for example, to a non-thermostable form of DNA polymerase.

BRIEF DESCRIPTION OF FIGURES

Particular non-limiting embodiments of the present invention will now be described with reference to the following Figures, in which.

EXAMPLES

Figures 1, 2:
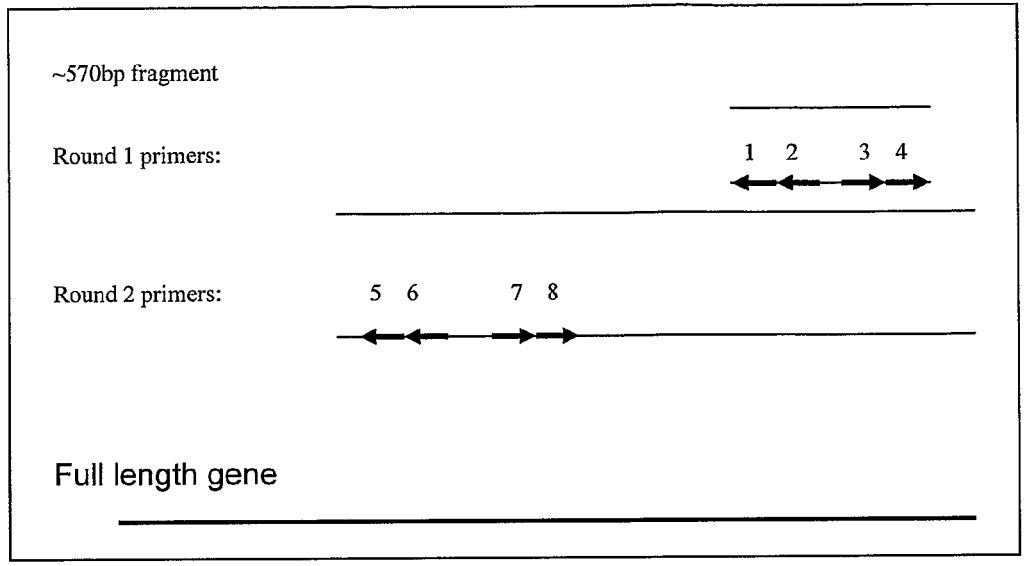
FIG. 1 is a diagram illustrating a gene walking method employed in cloning a novel DNA polymerase from *Thermodesulfatator indicus* according to one embodiment of the invention.
FIG. 2 is a diagram showing the structure of a new pET24a (+)HIS region used in cloning of the *T. indicus* DNA polymerase.

Agar-plated cultures of *Thermodesulfatator indicus* were obtained from the Deutsche Sammlung von Mikroorganismen and Zellkulturen GmbH (German Collection of Microorganisms and Cell Cultures; Accession No. DSM 15286). As described below, following extraction and amplification of gDNA from the cultures, a gene walking method was used as outlined below to reach the predicted 5' start and the 3' stop of DNA polymerase A gene ("DNA polA", encoding DNA polymerase I). A Large (or Klenow) fragment of the DNA polymerase I was found to be highly efficient in both PCR and LAMP reactions.

Example 1

Genomic DNA Extraction

The method for genomic DNA extraction from *T. indicus* cultures was derived from Gotz et al. (2002; Int. J. Syst. Evol. Microbiol. 52: 1349-1359) which is a modification of a method described in Ausubel et al. (1994; Current Protocols in Molecular Biology, Wiley, New York).

Cell pellets were resuspended in 567 μl 1× TE buffer (10 mM Tris/HCl, pH8.0; 1 mM EDTA), 7.5% Chelex 100 (Sigma), 50 mM EDTA (pH7.0), 1% (w/v) SDS and 200 μg Proteinase K and incubated with slow rotation for 1 h at 50° C. Chelex was removed by centrifugation. Then 100 μl M NaCl and 80 μl 10% (w/v) cetyltrimethylammonium bromide in 0.7M NaCl were added to the cell lysate and the sample incubated for 30 mins at 65° C. The DNA was extracted with phenol/chloroform, isopropanol precipitated and the DNA resuspended in water. DNA concentration was estimated on a 1% agarose gel.

Example 2

Initial Screening for DNA polA Gene

The screening method was derived from Shandilya et al. (2004, Extremophiles 8: 243-251).

Using degenerate polA primers PolATF1 and PolATR (see below), a ~570 bp fragment was amplified from 10 ng *T. indicus* gDNA.

The PolATF1 primer has the sequence:

```
5'-CATTTTTGCTGCCGATTAywsncarathga-3';        (SEQ ID NO: 5)
``` and the PolATR primer has the sequence:

```
5'-AACCGCGAAGTTTTTATTyragyagyac-3'.          (SEQ ID NO: 6)
```

The PCR reaction mix was as follows:

| | |
|---|---|
| 10x PCR Buffer (750 mM Tris-HCl, pH 8.8, 200 mM (NH₄)₂SO₄, 0.1% (v/v) Tween-20) | 10 μl |
| 5 mM dNTP's | 2 μl |
| 5' primer (10 pM/μl) | 2.5 μl |
| 3' primer (10 pM/μl) | 2.5 μl |
| gDNA | 10 ng |
| Taq DNA Polymerase (5 u/μl) | 0.25 μl |
| Water | To 50 μl. |

PCR cycling conditions were 4 minute initial denaturation at 94° C. followed by 45 cycles of: 10 seconds denaturation at 94° C., 30 seconds annealing at 42° C., 30 second extension at 72° C. Final extension at 72° C. for 7 mins. 4° C. hold.

A ~570 bp amplified product was TA cloned (Invitrogen pCR2.1 kit. Cat#1(2000-01) and sequenced using M13 Forward (5'-TGT AAA ACG ACG GCC AGT-3') (SEQ ID NO:7) and Reverse (5'-AGC GGA TAA CAA TTT CAC ACA GGA-3') (SEQ ID NO:8) primers on an ABI-3100 DNA sequencer. Sequencing data confirmed the fragment was DNA polymerase A (DNA polA) gene.

Example 3

DNA polA Gene Walking

From the amplification product obtained in Example 2, primers were designed to 'walk along' *T. indicus* gDNA to reach the 5' start and 3' stop of the DNA polA gene.

10 ng gDNA was digested individually with 5u of various 6 base pair-cutter restriction endonucleases in 10 μl reaction volume and incubated for 3 h at 37° C. 12 individual digest reactions were run, using a unique 6-cutter restriction enzyme (RE) for each. 5 μl digested template was then self-ligated using 12.5u T4 DNA Ligase, 1 μl 10× ligase buffer in 50 μl reaction volume, with an overnight incubation at 16° C.

Self-ligated DNA was then used as template in two rounds of PCR. As illustrated in FIG. 1, the first round of PCR employed primers 2 and 3 (see below), while a second round (nested-round) used primers 1 and 4 (see below) to give specificity to amplification.

First Round PCR:

The first round PCR reaction mix was as follows:

| | |
|---|---|
| Self-ligation reaction (~100 pg/μl DNA) | 2 μl |
| 10x PCR Buffer (200 mM Tris-HCl, pH 8.8, 100 mM KCl, 100 mM (NH₄)₂SO₄, 1% (v/v) Triton X-100, 20 mM MgSO₄) | 5 μl |
| 5 mM dNTP's | 2 μl |
| Primer 2 | 25 pM |
| Primer 3 | 25 pM |
| Taq/Pfu (20:1) (5 u/μl) | 1.25 u |
| Water | To 50 μl. |

Cycling conditions were 4 minute initial denaturation at 94° C. followed by 35 cycles of: 10 seconds denaturation at 94° C., 10 seconds annealing at 55° C., 5 minute extension at 72° C. Final extension at 72° C. for 7 mins. 4° C. hold.

Primer 2 [15286__2_(pos.2085)] has the sequence:

```
5'-AATCAAGGTTTCATCTCCCG-3';                  (SEQ ID NO: 9)
``` and Primer 3 [15286__3_(pos.2453)] has the sequence:

```
5'-TATTCAGGGGACAGCCGCTG-3'.                  (SEQ ID NO: 10)
```

Second Round (Nested) PCR:

The second round PCR reaction mix was as follows:

| | |
|---|---|
| First round PCR reaction | 1 μl |
| 10x PCR Buffer (200 mM Tris-HCl, pH 8.8, 100 mM KCl, 100 mM (NH₄)₂SO₄, 1% (v/v) Triton X-100, 20 mM MgSO₄) | 5 μl |
| 5 mM dNTP's | 2 μl |
| Primer 1 | 25 pM |
| Primer 4 | 25 pM |
| Taq/Pfu (20:1) (5 u/μl) | 1.25 u |
| Water | To 50 μl. |

Cycling conditions were 4 minute initial denaturation at 94° C. followed by 25 cycles of: 10 seconds denaturation at 94° C., 10 seconds annealing at 55° C., 5 minute extension at 72° C. Final extension at 72° C. for 7 minutes. 4° C. hold.

Primer 1 [15286__1_(pos.2063)] has the sequence:

```
5'-TAATGGGCTAAAACTCGCAG-3';                  (SEQ ID NO: 11)
``` and Primer 4 [15286__4_(pos.2521)] has the sequence:

```
5'-AAGGCTTTGGGACAAGGATG-3'.                  (SEQ ID NO: 12)
```

Amplified PCR fragments were ExoSAP treated and sequenced using the nested primers to reveal further DNA polA sequence data from which new gene walking primers could be designed. Two further separate steps of gene walking were required to generate fragments reaching the start and end of the *T. indicus* DNA polA gene.

Further Gene Walking Step 1:

1st round PCR using Primers 2 and 3 (as above), followed by nested PCR using Primers 1 and 4 (as above).

PCR fragments between ~1.5 kb and ~2.5 kb were obtained from Hind III, Kpn I, and EcoR V digested/self-ligated reaction templates.

These fragments were sequenced using the nested primers (Primers 1 and 4). Sequencing of fragments reached the C-terminal STOP codon for DNA polA and gave a further ~1100 bp of sequence data towards the N-terminal. New gene walking primers were designed to walk towards the N-terminal.

Further Gene Walking Step 2:

1St round PCR using Primers 6 and 7 (see below), followed by nested PCR using Primers 5 and 8 (see below).

Primer 5 [15286_5_(pos.1036)] has the sequence:

```
5'-TCT CGC TTT GTT TTA ACC C-3';    (SEQ ID NO: 13)
```

Primer 6 [15286_6_(pos.1013)] has the sequence:

```
5'-CAT GCG TGG GAA AAT AGT A-3';    (SEQ ID NO: 14)
```

Primer 7 [15286_7_(pos.1008)] has the sequence:

```
5'-ACT TTA TCC GGG TCA AGA AC-3';   (SEQ ID NO: 15)
``` and Primer 8 [15286_8_(pos.941)] has the sequence:

```
5'-TTT CGT ATC ACT TTC AAG GTC-3'.  (SEQ ID NO: 16)
```

PCR fragments between ~750 bp and 2 kb were obtained from Hind III, P st I, and Kpn I digested/self-ligated reaction templates.

These fragments were sequenced using the nested primers (Primers 5 and 8). This sequence data showed the fragments reached the N-terminal ATG start codon for DNA polA.

Example 4

Amplification of Full Length ("FL") and Large (Klenow) Fragment ("LF") DNA polA

Based on the sequence data derived from the gene walking protocol described in Example 3, a start and stop for the Large (Klenow) fragment could be predicted (based on alignment with known DNA polA sequences, for example the Taq Klen-Taq fragment), allowing specific primers to be designed to amplify the entire Large fragment gene (~1.7 kb).

These specific primers were:

```
15286_FL_Upper(NdeI)
                                    (SEQ ID NO: 17)
5'-GTC CAC CAT ATG GCG CAG AAA AGC TTG TTT

CCT AAA AAA TTA CCA TTT AAA GAT GA-3';

15286_LF_Upper(NdeI)
                                    (SEQ ID NO: 18)
5'-CTT GAA CAT ATG GGC CTC TTA AAA GAA CTT CCA GCT AC-3';
and 15286_Lower(SalI)
                                    (SEQ ID NO: 19)
5'-AGC CCT GTC GAC GGA TCC GCC AGC TTA TGC

CTT TGC CTC TGC -3'.
```

Restriction sites (underlined in the above primer sequences) for NdeI or SalI, as noted above, were built into the primers to facilitate cloning into expression vectors.

Gene products were amplified using a high fidelity Phusion DNA polymerase (New England Biolabs).

The PCR reaction mix was as follows:

| | |
|---|---|
| 5x HF Phusion reaction Buffer | 20 μl |
| 5 mM dNTP's | 4 μl |
| Upper primer (FL or LF) | 25 pM |
| Lower primer | 25 pM |
| gDNA | 10 ng |
| Phusion DNA Polymerase (2 u/μl) | 0.5 μl |
| Water | To 100 μl. |

Cycling conditions were 30 seconds initial denaturation at 98° C. followed by 25 cycles of: 3 seconds denaturation at 98° C., 10 seconds annealing at 55° C., 1.5 minute extension at 72° C. Final extension at 72° C. for 7 mins. 4° C. hold.

Example 5 pET24a(+)HIS Vector Construction

The pET24a(+) vector (Novagen) was modified to add a 6×HIS tag upstream of NdeI site (see FIG. 2). The HIS tag was inserted between XbaI and BamHI sites as follows.

An overlapping primer pair, of which an upper primer (XbaI) has the sequence:

```
                                    (SEQ ID NO: 20)
5'-TTC CCC TCT AGA AAT AAT TTT GTT TAA CTT TAA GAA

GGA GAT ATA CTA TG CAC CA-3',
``` and a lower primer (BamHI) has the sequence:

```
                                    (SEQ ID NO: 21)
5'-GAA TTC GGA TCC GCT AGC CAT ATG GTG ATG GTG ATG

GTG CAT AGT ATA TCT CCT T-3'.
``` were amplified by PCR, RE digested and ligated into pET24a(+). The ligation reaction was transformed into E. coli TOP10F' (Invitrogen) and plated on Luria Broth plates plus kanamycin. Colonies were screened by PCR and verified by sequencing using T7 sequencing primers:

```
T7_Promoter:
5'-AAATTAATACGACTCACTATAGGG-3',     (SEQ ID NO: 22)

T7_Terminator:
5'-GCTAGTTATTGCTCAGCGG-3'.          (SEQ ID NO: 23)
```

Example 6

Cloning of Full Length and Large Fragment DNA polA

PCR products from Example 4 were purified using Promega Wizard purification kit and then RE digested using Nde I/Sal I. DNA was phenol/chloroform extracted, ethanol-precipitated and resuspended in water. The full length ("FL") and Large fragment ("LF") sequences were then each ligated into pET24a(+) and pET24a(+)HIS, between Nde I and Sal I, and electroporated into KRX cells (Promega). Colonies were screened by PCR using vector-specific T7 primers.

Example 7

Expression of Full Length and Large Fragment DNA Polymerases

Recombinant colonies from Example 6 were grown up overnight in 5 ml Luria Broth (including Kanamycin/Chloramphenicol). 50 ml Terrific Broth baffled shake flasks were inoculated by 1/100 dilution of overnight culture. Cultures were grown at 37° C., 275 rpm to $OD_{600}$~1 then brought down to 24° C. and induced with L-rhamnose to 0.1% final concentration, and IPTG to 10 mM final concentration. Cultures were incubated for a further 18 h at 24° C., 275 rpm. 10 ml of the culture was then harvested by centrifugation for 10 mins at 5,000×g and cells were resuspended in 1 ml Lysis buffer (50 mM Tris-HCl, pH8.0, 100 mM NaCl, 1 mM EDTA) and sonicated for 2 bursts of 30 s (40v) on ice. Samples were centrifuged at 5,000×g for 5 min and heat lysed at 70° C. for 20 min to denature background *E. coli* proteins. Samples were centrifuged and aliquots of supernatant were size fractionated on 8% SDS-PAGE.

Figure 3:
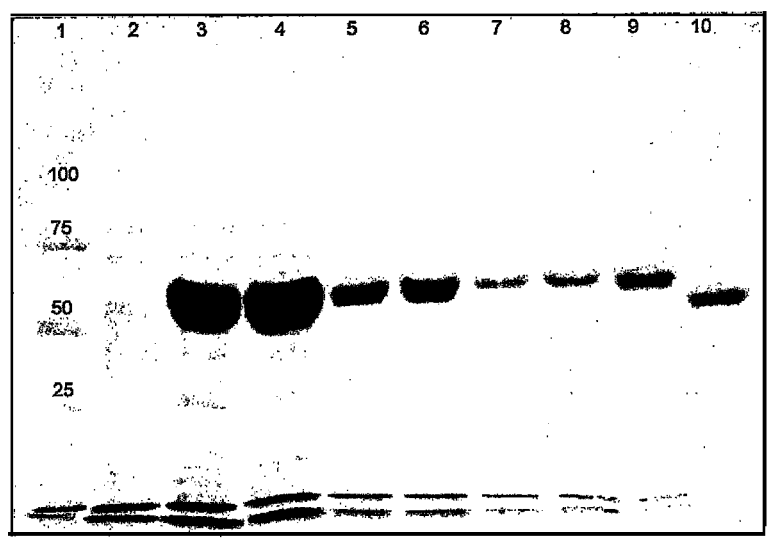
FIG. 3 is an SDS PAGE gel showing expression of Large fragments of the cloned *T. indicus* DNA polymerase. Lane 1 is a size marker, lane 2 is induced control with pET24a(+)HIS vector without insert, lane 3 is 100 µl *T. indicus* DNA polymerase, Large fragment with N-terminal HIS tag, lane 4 is 100 µl *T. indicus* DNA polymerase, Large fragment without N-terminal HIS tag, lane 5 is 20 µl *T. indicus* DNA polymerase, Large fragment with N-terminal HIS tag, lane 6 is 20 µl *T. indicus* DNA polymerase, Large fragment without N-terminal HIS tag, lane 7 is 50 *T. indicus* DNA polymerase, Large fragment with N-terminal HIS tag, lane 8 is 50 *T. indicus* DNA polymerase, Large fragment without N-terminal HIS tag, lane 9 is 50u *T. indicus* DNA polymerase, Large fragment with N-terminal HIS tag purified via single step chelating sepharose purification, and lane 10 is 12.5u KlenTaq DNA polymerase. Volumes refer to amount of protein loaded from that volume of induced *E. coli* KRX culture.

As shown in FIG. 3, *T. indicus* Large fragment DNA polymerase I was expressed at the predicted ~70 kDa.

Figure 4:
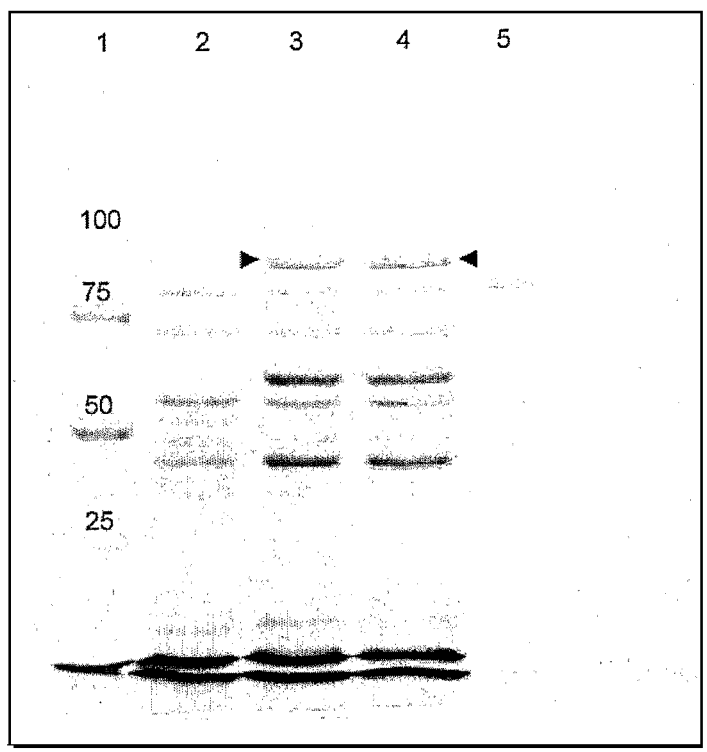
FIG. 4 is an SDS PAGE gel showing expression of full length embodiments of the cloned *T. indicus* DNA polymerase. Lane 1 is a size marker, lane 2 is induced Control with pET24a(+)HIS vector without insert, lane 3 is 100 µl *T. indicus* DNA Polymerase, full length with N-terminal HIS tag, lane 4 is 1000 *T. indicus* DNA Polymerase, full length without N-terminal HIS tag, and lane 5 is 25u Pfu DNA Polymerase. Volumes refer to amount of protein loaded from that volume of induced *E. coli* KRX culture.

FIG. 4 shows that *T. indicus* full length DNA polymerase I was expressed at the predicted ~103 kDa.

DNA polymerases are known to sometimes run slightly faster than expected on SDS PAGE gels, so that their apparent molecular weight is smaller than predicted.

Example 8

PCR Activity Assay

PCR activity of the samples obtained in Example 7 were tested in a 500 bp λDNA PCR assay. Taq DNA polymerase (1.25 u) was used as positive control.

The PCR solution contained:

| | |
|---|---|
| 10× PCR Buffer (750 mM Tris-HCl, pH 8.8, 200 mM $(NH_4)_2SO_4$, 0.1% (v/v) Tween-20) | 5 µl |
| 5 mM dNTP mix | 2 µl |
| Enzyme test sample | 1 µl |
| Upper λ primer | 25 pM |
| Lower λ primer | 25 pM |
| λDNA | 1 ng |
| Water | To 50 µl. |

The Upper λ primer has the sequence:

```
5'-GATGAGTTCGTGTCCGTACAACTGG-3',     (SEQ ID NO: 24)
``` while the Lower primer has the sequence:

```
5'-GGTTATCGAAATCAGCCACAGCGCC-3'.     (SEQ ID NO: 25)
```

PCR proceeded with 35 cycles of: 3 seconds denaturation at 94° C., 10 seconds annealing at 55° C., 30 seconds extension at 72° C. Final extension at 72° C. for 7 mins. 4° C. hold.

Figure 5:
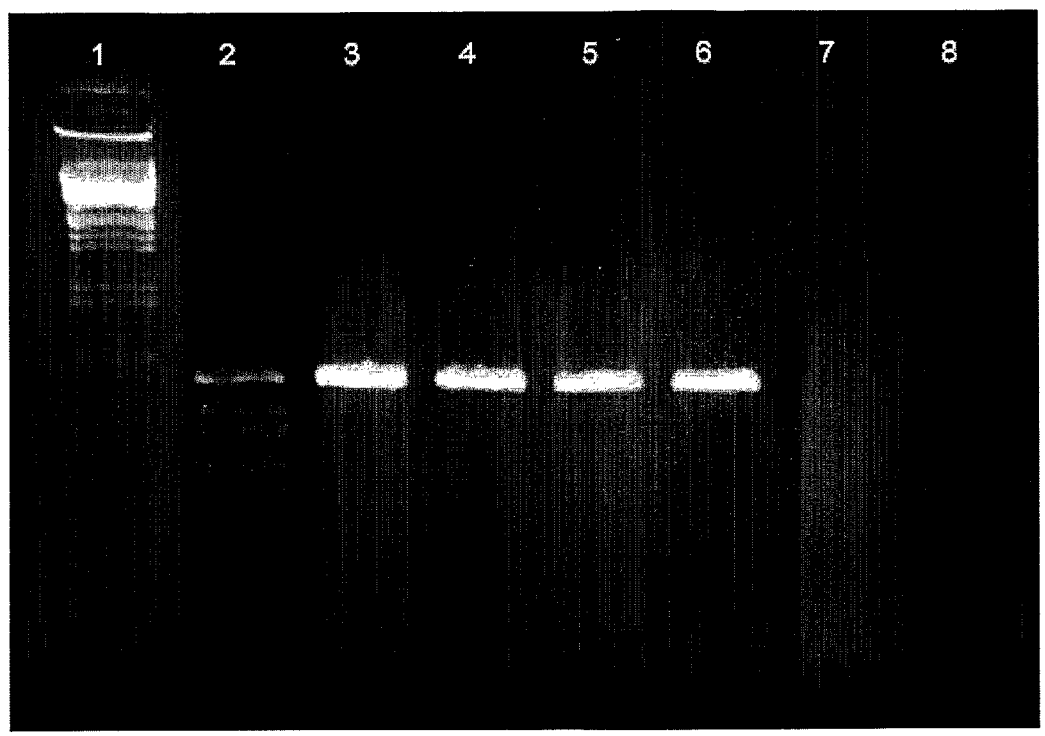
FIG. 5 is an agarose gel of PCR reaction samples showing amplification of lambda (λ) DNA using the cloned *T. indicus* DNA polymerase. Lane 1 is a lambda EcoR I/Hind III Size Marker, lane 2 is a 500 bp, 400 bp, 350 bp, 275 bp, 225 bp and 175 bp size marker, lane 3 shows amplification product using 1.25u Taq DNA polymerase, lane 4 shows 41 induced *T. indicus* DNA polymerase, Large fragment without N-terminal HIS tag, lane 5 shows 2 µl *T. indicus* DNA polymerase, Large fragment with N-terminal HIS tag, lane 6 shows 8 µl *T. indicus* DNA polymerase, Large fragment with N-terminal HIS tag and purified via single step chelating sepharose purification, lane 7 shows 10 µl *T. indicus* DNA polymerase, full length with N-terminal HIS tag, and lane 8 shows amplification product using induced pET24a(+)HIS vector lacking insert (as negative control). Volumes refer to amount of protein loaded from that volume of induced *E. coli* KRX culture.

An aliquot of the reaction products were run out on a 1.5% agarose gel, and the results are shown in FIG. 5. Under the PCR conditions used, the *T. indicus* Large fragment, both with and without an N-terminal HIS tag, showed comparable PCR activity to Taq DNA polymerase (lane 3), while the *T. indicus* full length DNA polymerase did not yield detectable PCR product (lane 7). Under the PCR assay conditions used here, Bst DNA polymerase did not yield any detectable PCR product (data not shown).

Example 9

LAMP Activity Assay

Samples obtained in Example 7 were also tested for loop-mediated isothermal amplification (LAMP) activity.

LAMP primers (see Nagamine et al., 2002) used were:

```
Lambda-FIP-LAMP ("FIP")
                                       (SEQ ID NO: 26)
5'-CAGCCAGCCGCAGCACGTTCGCTCATAGGAGATATGGTAGAGCCG
C-3';

Lambda-BIP-LAMP ("BIP")
                                       (SEQ ID NO: 27)
5'-GAGAGAATTTGTACCACCTCCCACCGGGCACATAGCAGTCCTAGG
GACAGT-3';

Lambda-F3-LAMP ("F3")
                                       (SEQ ID NO: 28)
5'-GGCTTGGCTCTGCTAACACGTT-3';

Lambda-B3-LAMP ("B3")
                                       (SEQ ID NO: 29)
5'-GGACGTTTGTAATGTCCGCTCC-3';

Lambda-loopF-LAMP ("loopF")
                                       (SEQ ID NO: 30)
5'-CTGCATACGACGTGTCT-3';
and Lambda-loopB-LAMP ("loopB")
                                       (SEQ ID NO: 31)
5'-ACCATCTATGACTGTACGCC-3'.
```

LAMP was performed in a total 25 µl reaction mixture containing 0.8 µM each of FIP and BIP, 0.2 µM each of F3 and B3, 0.4 µM each of loopF and loopB primers, 1.6 mM dNTPs, 1M betaine (Sigma), 2 mM $MgSO_4$, 1× Bst buffer (New England Biolabs), 1 ng λDNA, and either 8u Bst DNA polymerase large fragment (New England Biolabs; positive control) or 1 µl test sample (from Example 7), made up to volume with water. The mixture was incubated at 65° C. for 1 h and an aliquot run out on 1% agarose gel stained with ethidium bromide for detection of amplification.

Figure 6:
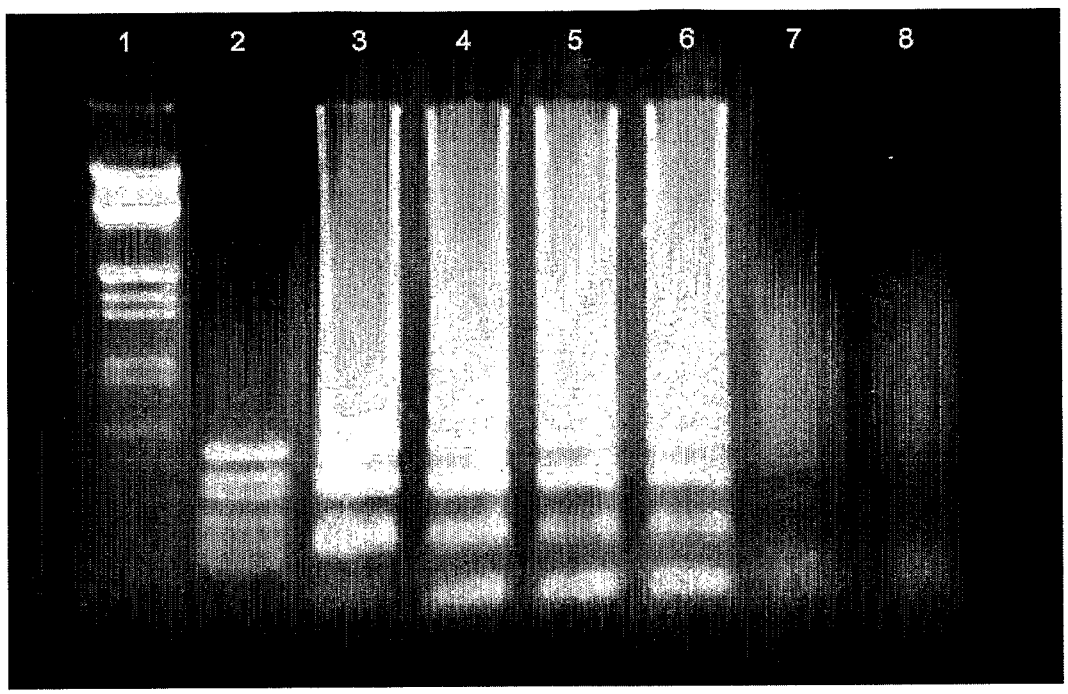
FIG. 6 is an agarose gel of LAMP reaction samples showing amplification results using the cloned *T. indicus* DNA polymerase. Lane 1 is a lambda EcoR I/Hind III Size Marker, lane 2 is a 500 bp, 400 bp, 350 bp, 275 bp, 225 bp and 175 bp size marker, lane 3 shows amplification product using 8u Bst DNA polymerase, Large fragment, lane 4 shows 2 µl *T. indicus* DNA polymerase, Large fragment without N-terminal HIS tag, lane 5 shows 2 µl *T. indicus* DNA polymerase, Large fragment with N-terminal HIS tag, lane 6 shows 8 µl *T. indicus* DNA polymerase, Large fragment with N-terminal HIS tag and purified via single step chelating sepharose purification, lane 7 shows 10 µl *T. indicus* DNA polymerase, full length with N-terminal HIS tag, and lane 8 shows amplification product using induced pET24a(+)HIS vector lacking insert (as negative control). Volumes refer to amount of protein loaded from that volume of induced *E. coli* KRX culture.

Results of the LAMP assay are shown in FIG. 6. Under the LAMP conditions used, the *T. indicus* Large fragment, both with and without an N-terminal HIS tag, showed comparable PCR activity to Bst DNA polymerase Large fragment (lane 3), while the *T. indicus* full length DNA polymerase did not yield detectable LAMP product (lane 7). It is possible that under these LAMP conditions, the full length DNA polymerase has 5'→3' exonuclease activity which destroys any LAMP amplification product. Under the LAMP assay conditions used here, Taq DNA polymerase did not yield any detectable LAMP product (data not shown).

Example 10

Thermostability Assay

Thermostability of the *T. indicus* Large fragment was tested using the 500 bp λDNA PCR assay as described above in Example 7. Samples of the induced Large fragment were incubated at 95° C. for 0, 2, 4, 6, 8, 10, 15 or 20 min, then used in the 500 bp DNA PCR assay. Under the conditions used, the Large fragment was found to be unaffected by up to 4 min incubation at 95° C., showed reduced PCR activity after 6 min incubation, and was unable to produce detectable PCR product after 8 min incubation (data not shown).

This example demonstrates that the *T. indicus* Large fragment was thermostable for a sufficient duration to be effective in PCR but that prolonged incubation at a denaturation temperature of 95° C. affected DNA polymerase activity.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

---

The invention claimed is:

1. An isolated polypeptide comprising artificially introduced amino acids at the N terminus and having at least 80% sequence identity to the amino acid sequence of SEQ ID NO: 1, wherein said polypeptide has thermostable DNA polymerase activity and exhibits strand displacement activity.

2. The isolated polypeptide of claim 1, wherein said polypeptide catalyses an isothermal amplification reaction and/or catalyses a thermocycling amplification reaction.

3. The isolated polypeptide of claim 1, wherein said polypeptide has at least 80% sequence identity to SEQ ID NO:32.

4. The isolated polypeptide of 1, wherein said polypeptide comprises the amino acid sequence of SEQ ID NO:32.

5. The isolated polypeptide of claim 1, wherein said polypeptide further comprises a Cren7 enhancer domain.

6. A composition comprising the isolated polypeptide of claim 1.

7. A kit comprising the isolated polypeptide of claim 1, and packaging materials therefor.

8. A kit comprising the composition of claim 6 and packaging materials therefor.

9. The isolated polypeptide of claim 1, wherein said polypeptide has at least 85% sequence identity to the amino acid sequence of SEQ ID NO: 1.

10. The isolated polypeptide of claim 9, wherein said polypeptide has at least 90% sequence identity to the amino acid sequence of SEQ ID NO: 1.

11. The isolated polypeptide of claim 10, wherein said polypeptide has at least 95% sequence identity to the amino acid sequence of SEQ ID NO: 1.

12. The isolated polypeptide of claim 1, wherein said polypeptide is obtained from a nucleic acid modified for expression in a host cell.

13. The isolated polypeptide of claim 12, wherein the nucleic acid is SEQ ID NO: 3 or SEQ ID NO: 33.

14. The isolated polypeptide of claim 1, wherein the artificially introduced amino acids at the N terminus comprise a dipeptide.

15. The isolated polypeptide of claim 14, wherein the dipeptide is MG.

* * * * *